(12) United States Patent
Takahashi et al.

(10) Patent No.: US 8,308,996 B2
(45) Date of Patent: Nov. 13, 2012

(54) CHROMENE COMPOUND

(75) Inventors: Toshiaki Takahashi, Shunan (JP); Junji Takenaka, Shunan (JP); Junji Momoda, Shunan (JP); Kazuhiro Teranishi, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

(21) Appl. No.: 13/386,920

(22) PCT Filed: Aug. 4, 2010

(86) PCT No.: PCT/JP2010/063592
§ 371 (c)(1),
(2), (4) Date: Jan. 25, 2012

(87) PCT Pub. No.: WO2011/016582
PCT Pub. Date: Feb. 10, 2011

(65) Prior Publication Data
US 2012/0121934 A1    May 17, 2012

(30) Foreign Application Priority Data
Aug. 4, 2009 (JP) ................................. 2009-181475

(51) Int. Cl.
*G02B 5/23* (2006.01)
*C07D 311/78* (2006.01)
*C07D 311/94* (2006.01)

(52) U.S. Cl. ..................... 252/586; 252/582; 428/411.1; 544/31; 544/79; 544/150; 546/167; 546/196; 549/24; 549/382

(58) Field of Classification Search .................. 252/582, 252/586; 428/411.1; 544/31, 79, 150; 546/167, 546/196; 549/24, 382
See application file for complete search history.

(56) References Cited

U.S. PATENT DOCUMENTS

| | | | | |
|---|---|---|---|---|
| 5,658,501 | A * | 8/1997 | Kumar et al. ................. | 252/586 |
| 6,146,554 | A | 11/2000 | Melzig et al. | |
| 6,296,785 | B1 | 10/2001 | Nelson et al. | |
| 6,723,859 | B2 | 4/2004 | Kawabata et al. | |
| 6,774,202 | B2 | 8/2004 | Lee | |
| 7,008,568 | B2 | 3/2006 | Qin | |
| 7,521,004 | B2 | 4/2009 | Momoda et al. | |
| 2006/0226402 | A1 | 10/2006 | Kim et al. | |
| 2009/0309076 | A1 | 12/2009 | He et al. | |
| 2011/0062396 | A1 | 3/2011 | Kasai et al. | |

FOREIGN PATENT DOCUMENTS

| | | | |
|---|---|---|---|
| WO | WO 99/15518 A1 | 4/1999 | |
| WO | WO 00/35902 | * | 6/2000 |
| WO | WO 00/35902 A1 | 6/2000 | |
| WO | WO 01/19813 A1 | 3/2001 | |
| WO | WO 01/19813 A1 | * | 3/2001 |
| WO | WO 01/60811 A1 | 8/2001 | |
| WO | WO 01/60881 A2 | 8/2001 | |
| WO | WO 03/044022 A2 | 5/2003 | |
| WO | WO 2005/028465 A1 | * | 3/2005 |
| WO | WO 2005/028465 A1 | 3/2005 | |
| WO | WO 2006/110513 A1 | 10/2006 | |
| WO | WO 2006/110513 A1 | * | 10/2006 |
| WO | WO 2009/136668 A1 | 11/2009 | |

OTHER PUBLICATIONS

Clive et al., "Formal Radical Cyclization Onto Benzene Rings: A general Method and Its Use in the Synthesis of ent-Nocardione A," The Journal of Organic Chemistry, vol. 69, 2004, pp. 3282-3203.
Gourdoupis, "A Direct and Versatile Synthesis of 5-(2-Di-n-Propylamino-Ethyl)-7-Methoxyindole," Synthetic Communications, vol. 23, No. 16, 1993, pp. 2241-2249.
International Preliminary Report on Patentability, and Translation of Written Opinion of the International Searching Authority, dated Mar. 22, 2012, for International Application No. PCT/JP2010/063592 (Forms PCT/IB/338, PCT/IB/373 and PCT/ISA/237).

* cited by examiner

*Primary Examiner* — Bijan Ahvazi
(74) *Attorney, Agent, or Firm* — Birch, Stewart, Kolasch & Birch, LLP

(57) ABSTRACT

A photochromic chromene compound which develops a color of a neutral tint, has high color optical density, a high fading speed and high durability, and has an indeno(2,1-f)naphtho(1,2-b)pyran structure represented by the following formula as the basic skeleton, wherein a sulfur-containing substituent selected from thiol group, alkylthio group, alkoxyalkylthio group, haloalkylthio group, cycloalkylthio group, arylthio group and heteroarylthio group is bonded to the 6-position and/or 7-position carbon atom(s).

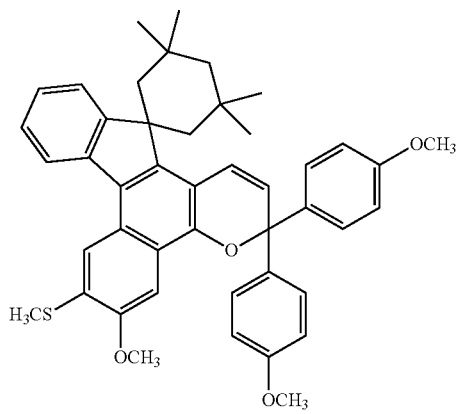

8 Claims, No Drawings

CHROMENE COMPOUND

TECHNICAL FIELD

The present invention relates to a novel chromene compound and an intermediate and use thereof. More specifically, it relates to a novel chromene compound which is useful as a photochromic compound for photochromic spectacle lenses and an intermediate and use thereof.

BACKGROUND ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (I) the degree of coloration at a visible light range before ultraviolet light is applied (initial coloration) should be low, (II) the degree of coloration upon exposure to ultraviolet light (to be referred to as "color optical density" hereinafter) should be high, (III) the speed from the time when the application of ultraviolet light is started to the time when the color optical density reaches saturation (to be referred to as "color development sensitivity" hereinafter) should be high; (IV) the speed from the stoppage of the application of ultraviolet light to the time when the compound returns to its original state (to be referred to as "fading speed" hereinafter) should be high, (V) the repeat durability of this reversible function should be high, and (VI) the solubility in a monomer composition which will become a host material after curing of the photochromic compound should be high so that its dispersibility in the host material in use becomes high.

As the photochromic compound which can satisfy these requirements, there are known chromene compounds having an indeno(2,1-f)naphtho(1,2-b)pyran structure as the basic skeleton (refer to a pamphlet of International Laid-Open WO99/15518 and a pamphlet of International Laid-Open WO2001/60811).

It is preferred that a photochromic plastic lens comprising the photochromic compound should develop a color of a neutral tint such as gray or brown. A color of a neutral tint is obtained by mixing together several different kinds of photochromic compounds which develop different colors. More specifically, it is obtained by mixing a yellow to red photochromic compound (yellow compound) having a maximum absorption at 430 to 530 nm with a purple to blue photochromic compound (blue compound) having a maximum absorption at 550 to 650 nm at the time of color development.

However, when color control is carried out by this method, various problems occur due to the difference in photochromic properties between the compounds which have been mixed together. For example, when the repeat durability of the yellow compound is lower than that of the blue compound and the photochromic plastic lens is used for a long time, the developed color gradually changes to a color with a strong blue tint.

When the color development sensitivity and fading speed of the yellow compound are lower than those of the blue compound, there occurs a problem that the color during color development has a strong blue tint and the color during fading has a strong yellow tint.

It is considered that this problem can be solved by using a compound which has two or more absorption maximums at the time of exposure and develops a color of a neutral tint by itself (double peak compound). It is known that a yellow compound is generally inferior to a blue compound in durability. Therefore, a compound having a higher yellow color optical density (having a maximum absorption wavelength at 430 to 530 nm) than the blue color optical density (having a maximum absorption wavelength at 550 to 650 nm) is desired as the double peak compound (the ratio of the yellow color optical density to the blue color optical density in the double peak compound may be referred to as "double peak characteristic" hereinafter).

As the photochromic compound having two or more absorption maximums at the time of color development (double peak compound), there are known compounds represented by the following formulas (A) to (D).

However, these compounds have room for the improvement of the following points. That is, a chromene compound represented by the following formula (A) (refer to a pamphlet of International Laid-Open WO01/19813) has a low fading speed and low repeat durability though its double peak characteristic is high.

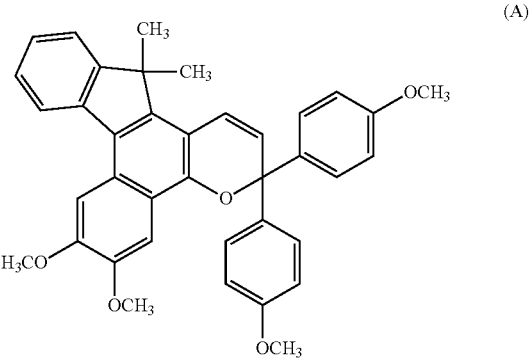

(A)

A chromene compound represented by the following formula (B) (refer to a pamphlet of International Laid-Open WO03/044022) has smaller absorption at 430 to 530 nm than absorption at 550 to 650 nm and low double peak characteristic.

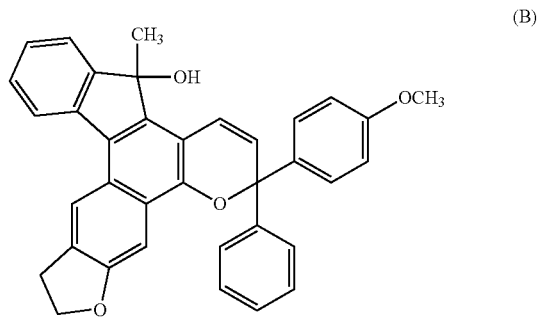

(B)

Although a chromene compound represented by the following formula (C) (refer to a pamphlet of International Laid-Open WO05/028465) has excellent double peak characteristic and practical levels of color optical density and fading speed, the end of its absorption spectrum (to be referred to as "absorption end" hereinafter) goes beyond 420 nm into the visible range. Therefore, it has room for improvement because its initial coloration is slightly large.

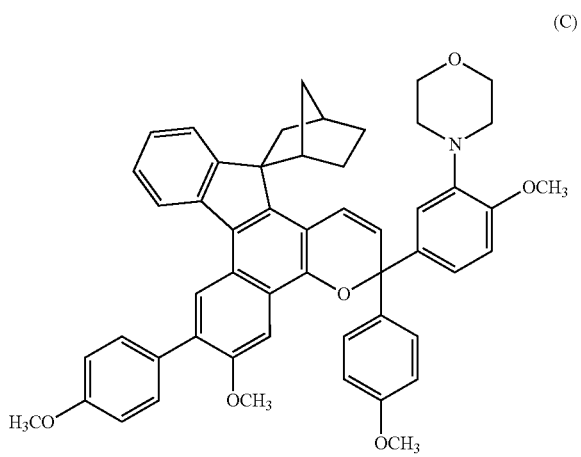

Further, US2009/0309076A1 discloses a chromene compound represented by the following formula (D). However, the compound has room for improvement as its absorption at 430 to 530 nm is smaller than absorption at 550 to 650 nm and its double peak characteristic is low.

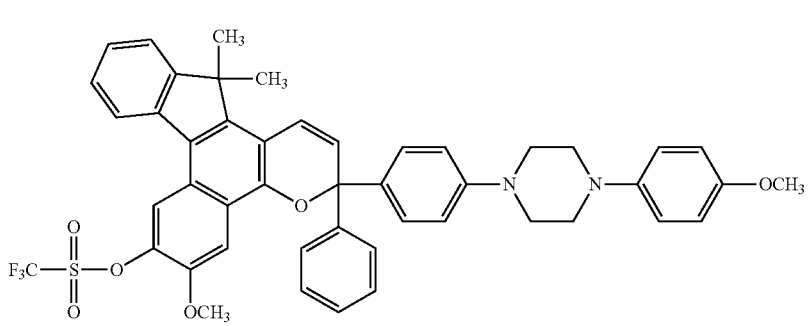

DISCLOSURE OF THE INVENTION

It is therefore an object of the present invention to provide a chromene compound which develops a color of a neutral tint and has much improved photochromic properties as compared with the above compounds.

It is another object of the present invention to provide a chromene compound which has little initial coloration, high color optical density and a high fading speed, is rarely colored at the time of deterioration and rarely experiences a reduction in color optical density when it is used repeatedly, that is, excellent durability of photochromic properties.

It is still another object of the present invention to provide a chromene compound which can dissolve in a monomer composition which will become a substrate of an optical article in a high concentration.

It is a further object of the present invention to provide a novel naphthol compound for the manufacture of the chromene compound of the present invention.

Other objects and advantages of the present invention will become apparent from the following description.

It is known that, in the indeno(2,1-f)naphtho(1,2-b)pyran skeleton which is known to provide excellent photochromic properties, the double peak characteristic is improved, the absorption end can be positioned at a short wavelength range and the initial coloration can be reduced by enhancing the electron donating ability of the 6-position and/or 7-position substituent(s) (introducing an electron donor group having a Hammett constant $\sigma_p$ of less than 0) whereas the fading speed becomes lower, the color development by heat at room temperature under no exposure (this color development will be referred to as "initial coloration by thermochromism" hereinafter) becomes larger and the durability becomes lower as the electron donating ability of the 6-position and/or 7-position substituent(s) becomes higher.

The inventors of the present invention have conducted intensive studies to solve the above problems and have found that a chromene compound which has high double peak characteristic, not so low fading speed and little initial coloration by thermochromism though the electron donating ability of the substituent (a Hamett constant $\sigma_p$ close to 0) is low is obtained when a specific substituent containing a sulfur atom is introduced into the 6-position and/or 7-position of the indeno(2,1-f)naphtho(1,2-b)pyran structure. The present invention has been accomplished based on this finding.

That is, firstly, the present invention is a chromene compound having a skeleton represented by the following formula (1).

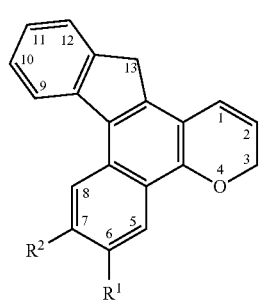

In the above formula, (i) $R^1$ and $R^2$ are each a sulfur-containing substituent selected from the group consisting of thiol group, alkylthio group, alkoxyalkylthio group, haloalkylthio group, cycloalkylthio group, arylthio group and heteroarylthio group, (ii) $R^1$ is the above sulfur-containing substituent and $R^2$ is a hydrogen atom, hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group, or (iii) $R^2$ is the above sulfur-containing substituent and $R^1$ is a hydrogen atom, hydroxyl group, alkyl group, haloalkyl group, cycloalkyl group, alkoxy group, amino group, aliphatic heterocyclic group having a ring member nitrogen atom and bonded to the benzene ring to which the aliphatic heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group or aryloxy group.

Secondly, the present invention is a photochromic curable composition comprising the chromene compound of the present invention and polymerizable monomers.

Thirdly, the present invention is a photochromic optical article having a polymer molded product containing the chromene compound of the present invention dispersed therein as a constituent member. In the fourth place, the present invention is an optical article having an optical substrate all or part of at least one surface of which is coated with a polymer film containing the chromene compound of the present invention dispersed therein as a constituent member.

Finally, the present invention is a naphthol compound represented by the formula (7) which will be given hereinafter.

BEST MODE FOR CARRYING OUT THE INVENTION

The chromene compound of the present invention has an indeno(2,1-f)naphtho(1,2-b)pyran structure represented by the above formula (1) as the basic skeleton. It is known that chromene compounds having an indeno(2,1-f)naphtho(1,2-b)pyran structure as the basic skeleton exhibit excellent photochromic properties. Out of the chromene compounds having the above basic skeleton, the chromene compound of the present invention can develop a dark or strong color of a neutral tint by itself while retaining its excellent photochromic properties by introducing a specific substituent into the 6-position and/or 7-position carbon atom(s). The specific substituent is a sulfur-containing substituent selected from the group consisting of thiol group, alkylthio group, alkoxyalkylthio group, haloalkylthio group, cycloalkylthio group, arylthio group and heteroarylthio group. A chromene compound having a specific substituent introduced into the specific position(s) has been unknown. The above substituent introduced into the 6-position and/or the 7-position of the pyran structure may be simply referred to as "sulfur-containing substituent" hereinafter. A description is subsequently given of this sulfur-containing substituent.

<$R^1$ and $R^2$>

$R^1$ and $R^2$ are any one of the combinations (i), (ii) and (iii) as described above.

When $R^1$ and $R^2$ are the combination (i), there is obtained the chromene compound of the present invention which is particularly notable in that it is excellent in double peak characteristic and durability and has little initial coloration due to the positioning of the absorption end at a short wavelength range and the reduction of thermochromism as well as a high fading speed.

When $R^1$ and $R^2$ are the combination (ii), there is obtained the chromene compound of the present invention which is particularly notable in that it is excellent in double peak characteristic and durability and has little initial coloration due to the positioning of the absorption end at a short wavelength range.

Further, when $R^1$ and $R^2$ are the combination (iii), there is obtained the chromene compound of the present invention which is particularly notable in that it is excellent in double peak characteristic and durability and has little initial coloration due to the reduction of thermochromism.

In the above combinations (i), (ii) and (iii), $R^1$ which is a substituent bonded to the 6-position carbon atom of the pyran skeleton and/or $R^2$ which is a substituent bonded to the 7-position carbon atom of the pyran skeleton are/is a sulfur-containing substituent selected from the group consisting of thiol group, alkylthio group, alkoxyalkylthio group, haloalkylthio group, cycloalkylthio group, arylthio group and heteroarylthio group.

The above alkylthio group is preferably an alkylthio group having 1 to 6 carbon atoms. Preferred examples of the alkylthio group include methylthio group, ethylthio group, n-propylthio group, isopropylthio group, n-butylthio group, sec-butylthio group and t-butylthio group.

The above alkoxyalkylthio group is preferably an alkylthio group having 1 to 6 carbon atoms and substituted by an alkoxy group having 1 to 3 carbon atoms. Preferred examples of the alkoxyalkylthio group include methoxymethylthio group, methoxyethylthio group, methoxy n-propylthio group, methoxy n-butylthio group, ethoxyethylthio group and n-propoxypropylthio group.

The above haloalkylthio group is preferably an alkyl group having 1 to 6 carbon atoms and substituted by a fluorine atom, chlorine atom or bromine atom. Preferred examples of the haloalkylthio group include trifluoromethylthio group, tetrafluoroethylthio group, chloromethylthio group, 2-chloroethylthio group and bromomethylthio group.

The above cycloalkylthio group is preferably a cycloalkylthio group having 3 to 8 carbon atoms. Preferred examples of the cycloalkylthio group include cyclopropylthio group, cyclobutylthio group, cyclopentylthio group and cyclohexylthio group.

The above arylthio group is preferably an arylthio group having 6 to 10 carbon atoms. Preferred examples of the arylthio group include phenylthio group, 1-naphthylthio group and 2-naphthylthio group.

The above heteroarylthio group is preferably a heteroarylthio group having 4 to 12 carbon atoms. Preferred examples of the heteroarylthio group include thienylthio group, furylthio group, pyrrolylthio group, pyridylthio group, benzothienylthio group, benzofurylthio group and benzopyrrolylthio group.

One to nine hydrogen atoms, particularly preferably one to four hydrogen atoms of each of the above arylthio group and the above heteroarylthio group may be substituted by an alkyl group having 1 to 6 carbon atoms, an alkoxy group having 1 to 6 carbon atoms, a cycloalkyl group having 3 to 8 carbon atoms, or a halogen atom.

As the above sulfur-containing substituent, an alkylthio group having 1 to 6 carbon atoms, an alkylthio group having 1 to 6 carbon atoms and substituted by an alkoxy group having 1 to 3 carbon atoms, or a cycloalkylthio group having 3 to 8 carbon atoms is preferred from the viewpoints of increasing color optical density and double peak characteristic and reducing initial coloration by positioning the absorption end at a short wavelength range and reducing thermochromism. Further, an alkylthio group having 1 to 6 carbon atoms or a cycloalkylthio group having 3 to 8 carbon atoms is particularly preferred from the viewpoints of increasing color optical density and double peak characteristic in particular. Particularly preferred examples of these groups include methylthio group, ethylthio group and cyclohexylthio group.

A thiol group or a haloalkylthio group having 1 to 6 carbon atoms is preferred from the viewpoints of increasing the fading speed and reducing initial coloration by thermochromism. Further, a haloalkylthio group having 1 to 6 carbon atoms is particularly preferred. More specifically, a trifluoromethylthio group is particularly preferred.

In the above combination (ii), $R^2$ is a hydrogen atom, hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group may be a primary amino group, or a secondary amino group or tertiary amino group having a substituent. Examples of the substituent of the amino group include alkyl group having 1 to 6 carbon atoms, haloalkyl group having 1 to 6 carbon atoms, alkoxy group having 1 to 6 carbon atoms, cycloalkyl group having 3 to 7 carbon atoms, aryl group having 6 to 14 carbon atoms and heteroaryl group having 4 to 14 carbon atoms. Preferred examples of the amino group include amino group, methylamino group, dimethylamino group, ethylamino group, diethylamino group, phenylamino group and diphenylamino group.

Preferred examples of the above heterocyclic group having a ring member nitrogen atom and bonded to the benzene ring to which the heterocyclic group bonds via the nitrogen atom include aliphatic heterocyclic groups such as morpholino group, piperidino group, pyrrolidinyl group, piperazino group and N-methylpiperazino group, and aromatic heterocyclic groups such as indolinyl group.

Preferred examples of the above alkylcarbonyl group include acetyl group and ethylcarbonyl group.

Preferred examples of the above alkoxycarbonyl group include methoxycarbonyl group and ethoxycarbonyl group.

Examples of the halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

These aralkyl group, aralkoxy group, aryloxy group and aryl group may be obtained by substituting 1 to 7 hydrogen atoms, particularly preferably 1 to 4 hydrogen atoms of a benzene ring or a naphthalene ring by the above hydroxyl group, alkyl group, haloalkyl group, cycloalkyl group, alkoxy group, amino group, heterocyclic group, cyano group, nitro group, formyl group, hydroxycarbonyl group, alkylcarbonyl group, alkoxycarbonyl group or halogen atom.

When $R^2$ is a hydroxyl group, alkyl group, cycloalkyl group, alkoxy group, amino group, heterocyclic group having a ring member nitrogen atom and bonded to the benzene ring to which the heterocyclic group bonds via the nitrogen atom, aralkyl group, aralkoxy group, aryloxy group or aryl group, the double peak characteristic becomes higher than when $R^2$ is a group other than these. Out of these, $R^2$ is preferably a hydroxyl group, alkoxy group, amino group, heterocyclic group having a ring member nitrogen atom and bonded to a benzene ring bonded thereto via the nitrogen atom or aryloxy group from the viewpoints of increasing double peak characteristic and color optical density and reducing initial coloration by positioning the absorption end at a short wavelength range. It is particularly preferably an alkoxy group or heterocyclic group having a ring member nitrogen atom and bonded to a benzene ring bonded thereto via the nitrogen atom. More specifically, it is particularly preferably a methoxy group or morpholino group.

Further, in the above combination (iii), $R^1$ is a hydrogen atom, hydroxyl group, alkyl group, haloalkyl group, cycloalkyl group, alkoxy group, amino group, aliphatic heterocyclic group having a ring member nitrogen atom and bonded to the benzene ring to which the aliphatic heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group or aryloxy group. Examples of the alkyl group, haloalkyl group, cycloalkyl group, alkoxy group, amino group, aliphatic heterocyclic group having a ring member nitrogen atom and bonded to the benzene ring to which the aliphatic heterocyclic group bonds via the nitrogen atom, alkylcarbonyl group, alkoxycarbonyl group, halogen atom, aralkyl group, aralkoxy group and aryloxy group out of these are the same as those enumerated for $R^2$ in the above combination (ii).

When $R^1$ is a hydroxyl group, alkyl group, cycloalkyl group, alkoxy group, amino group, aliphatic heterocyclic group having a ring member nitrogen atom and bonded to the benzene ring to which the aliphatic heterocyclic group bonds via the nitrogen atom, aralkyl group, aralkoxy group or aryloxy group, the double peak characteristic becomes higher than when $R^1$ is a group other than these. Out of these, $R^1$ is preferably a hydroxyl group, alkoxy group, amino group, heterocyclic group having a ring member nitrogen atom and bonded to the benzene ring bonded thereto via the nitrogen atom or aryloxy group from the viewpoints of increasing double peak characteristic and color optical density. It is more preferably an alkoxy group or heterocyclic group having a ring member nitrogen atom and bonded to the benzene ring to which the heterocyclic group bonds via the nitrogen atom. It is particularly preferably a methoxy group or morpholino group.

<Preferred Chromene Compound>

Out of the chromene compounds of the present invention, a chromene compound represented by the following formula (2) is preferred as it develops a color of a neutral tint and has high color optical density, a high fading speed and excellent durability of photochromic properties.

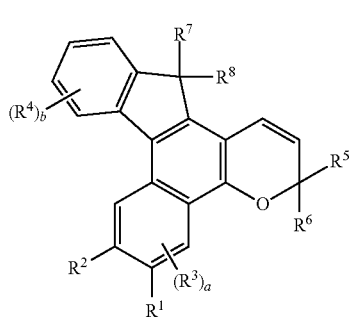

(2)

The substituent of the chromene compound represented by the above formula (2) will be described.

<$R^1$ and $R^2$>

$R^1$ and $R^2$ are as defined in the above formula (1). When $R^1$ and $R^2$ are the combination (i), $R^1$ and $R^2$ may be the same or different.

<$R^3$ and $R^4$>

$R^3$ and $R^4$ are each independently a hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group may be a primary amino group, or a secondary amino group or tertiary amino group having a substituent. Examples of the substituent of the amino group include alkyl group having 1 to 6 carbon atoms, haloalkyl group having 1 to 6 carbon atoms, alkoxy group having 1 to 6 carbon atoms, cycloalkyl group having 3 to 7 carbon atoms, aryl group having 6 to 14 carbon atoms and heteroaryl group having 4 to 14 carbon atoms. Preferred examples of the amino group include amino group, methylamino group, dimethylamino group, ethylamino group, diethylamino group, phenylamino group and diphenylamino group.

Examples of the above heterocyclic group having a ring member nitrogen atom and bonded to the benzene ring to which the heterocyclic group bonds via the nitrogen atom include aliphatic heterocyclic groups such as morpholino group, piperidino group, pyrrolidinyl group, piperazino group and N-methylpiperazino group, and aromatic heterocyclic groups such as indolinyl group.

Preferred examples of the above alkylcarbonyl group include acetyl group and ethylcarbonyl group.

Preferred examples of the above alkoxycarbonyl group include methoxycarbonyl group and ethoxycarbonyl group.

Examples of the halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

One to seven hydrogen atoms, particularly preferably one to four hydrogen atoms of the benzene or naphthalene ring of each of the above aralkyl group, aralkoxy group, aryloxy group and aryl group may be substituted by the above hydroxyl group, alkyl group, haloalkyl group, cycloalkyl group, alkoxy group, amino group, heterocyclic group, cyano group, nitro group, formyl group, hydroxycarbonyl group, alkylcarbonyl group, alkoxycarbonyl group or halogen atom.

"a" is an integer of 0 to 2 and indicates the number of $R^3$'s. When "a" is 2, two $R^3$'s may be the same or different. "b" is an integer of 0 to 4 and indicates the number of $R^4$'s. When "b" is an integer of 2 to 4, a plurality of $R^4$'s may be the same or different.

Particularly preferably, $R^3$ has a stereoscopically small substituent as a high fading speed is obtained. Therefore, particularly preferred $R^3$ is a hydrogen atom ("a" is 0).

Meanwhile, $R^4$ is preferably a hydrogen atom ("b" is 0), haloalkyl group or cyano group as a high fading speed is obtained, particularly preferably a hydrogen atom, trifluoromethyl group or cyano group. $R^4$ is preferably bonded to the 11-position carbon atom to obtain a higher fading speed.

When a plurality of $R^3$'s and a plurality of $R^4$'s are existent, preferred $R^3$'s and $R^4$'s are the same as those enumerated above.

<$R^5$ and $R^6$>

$R^5$ and $R^6$ are each independently a group represented by the following formula (3), group represented by the following formula (4), aryl group, heteroaryl group or alkyl group.

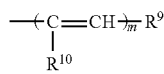

(3)

(4)

In the above formula (3), $R^9$ is an aryl group or heteroaryl group. Examples of the aryl group are the same as those enumerated for $R^3$ and $R^4$. The heteroaryl group is preferably a heteroaryl group having 4 to 12 carbon atoms. Preferred examples of the heteroaryl group include thienyl group, furyl group, pyrrolyl group, pyridyl group, benzothienyl group, benzofuryl group and benzopyrrolyl group.

$R^{10}$ is a hydrogen atom, alkyl group or halogen atom. Preferred examples of the alkyl group include methyl group, ethyl group and propyl group. Examples of the halogen atom are fluorine atom, chlorine atom, bromine atom and iodine atom.

"m" is an integer of 1 to 3. From the viewpoint of the acquisition of the raw material, "m" is preferably 1.

Preferred examples of the group represented by the above formula (3) include phenyl-ethylenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N,-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (4), $R^{11}$ is an aryl group or heteroaryl group. It is understood that these groups are the same as $R^9$. "n" is an integer of 1 to 3. From the viewpoint of the easy acquisition of the raw material, "n" is preferably 1.

Preferred examples of the group represented by the above formula (4) include phenyl-ethylinyl group, (4-(N,N-dimethylamino)phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethyl group, 2-benzofuranyl-ethynyl group and 2-(N-methyl)indolyl-ethynyl group, Examples of the aryl group, heteroaryl group and alkyl group represented by $R^5$ and $R^6$ are the same as those enumerated for $R^3$, $R^4$ and $R^9$.

$R^5$ and $R^6$ may form an aliphatic hydrocarbon ring together with the carbon atom to which $R^5$ and $R^6$ bond.

Preferred examples of the aliphatic hydrocarbon ring include adamantane ring, bicyclononane ring, norbornane ring and fluorene ring.

For the chromene compound of the above formula (2) to exhibit excellent photochromic properties (double peak characteristic and fading speed), at least one, preferably both of the above $R^5$ and $R^6$ are preferably aryl groups or heteroaryl groups. Further, at least one, preferably both of $R^5$ and $R^6$ are particularly preferably any one of the groups (iv) to (vii):

(iv) an aryl group or heteroaryl group having an alkyl group or alkoxy group as a substituent;

(v) an aryl group or heteroaryl group having an amino group as a substituent;

(vi) an aryl group or heteroaryl group having a heterocyclic group having a nitrogen atom as a ring member hetero atom and bonded to an aryl group or heteroaryl group via the nitrogen atom as a substituent; or (vii) an aryl group or heteroaryl group having, as a substituent, a condensed heterocyclic group which is a heterocyclic group in the above (vi) condensed with an aromatic hydrocarbon ring or aromatic heterocyclic ring.

Although the positions and total number of substituents substituting the aryl groups in (iv) to (vii) are not particularly limited, to exhibit excellent photochromic properties, when the aryl group is a phenyl group, the position of the substituent is 3-position or 4-position, and the number of substituents in this case is preferably 1. Preferred examples of the aryl group include 4-methylphenyl group, 4-methoxyphenyl group, 3,4-dimethoxyphenyl group, 4-n-propoxyphenyl group, 4-(N,N-dimethylamino)phenyl group, 4-(N,N-diethylamino)phenyl group, 4-(N,N-diphenylamino)phenyl group, 4-morpholinophenyl group, 4-piperidinophenyl group, 3-(N,N-dimethylamino)phenyl group and 4-(2,6-dimethylpiperidino)phenyl group.

Although the positions and total number of substituents substituting the heteroaryl groups in (iv) to (vii) are not particularly limited, the number of the substituents is preferably 1. Preferred examples of the heteroaryl group include 4-methoxythienyl group, 4-(N,N-dimethylamino)thienyl group, 4-methylfuryl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuranyl group.

<$R^7$ and $R^8$>

$R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group.

Examples of the above alkyl group, haloalkyl group, cycloalkyl group, alkoxy group, alkylcarbonyl group, alkoxycarbonyl group, halogen atom, aralkyl group, aralkoxy group, aryloxy group and aryl group are the same as those enumerated for $R^3$ and $R^4$.

Preferred examples of the above alkoxyalkyl group include methoxymethyl group, methoxyethyl group, methoxyn-propyl group, methoxyn-butyl group, ethoxyethyl group and n-propoxypropyl group.

$R^7$ and $R^8$ may form an aliphatic ring having 3 to 20 ring member carbon atoms, condensed poly-ring having an aromatic ring or aromatic hetero ring condensed to the aliphatic ring, hetero ring having 3 to 20 ring member atoms, or condensed poly-ring having an aromatic ring or aromatic hetero ring condensed to the hetero ring, together with the 13-position carbon atom to which $R^7$ and $R^8$ bond.

Examples of the above aliphatic ring include cyclopentane ring, cyclohexane ring, cyclooctane ring, cycloheptane ring, norbornane ring, bicyclononane ring and adamantane ring.

The condensed poly-ring having an aromatic ring or aromatic hetero ring condensed to the aliphatic ring is, for example, a phenanthrene ring.

Examples of the above hetero ring include thiophene ring, furane ring and pyridine ring.

Examples of the above condensed poly-ring having an aromatic ring or aromatic hetero ring condensed to the above hetero ring include phenylfuran ring and biphenylthiophene ring.

<Particularly Preferred $R^7$ and $R^8$>

In the present invention, preferred substituents of $R^7$ and $R^8$ are each a hydroxyl group, alkyl group or alkoxy group, or form a ring together with the 13-position carbon atom bonded thereto. An example of the alkyl group is methyl group and an example of the alkoxy group is methoxy group. To reduce initial coloration by thermochromism and increase the fading speed while retaining high double peak characteristic, substituents of $R^7$ and $R^8$ preferably form a ring together with the 13-position carbon atom bonded thereto. More preferably, they form the above aliphatic ring or the condensed poly-ring having an aromatic ring or aromatic hetero ring condensed to the above aliphatic ring from the viewpoint of increasing the fading speed. Particularly preferably, they form the above aliphatic ring from the viewpoint of reducing initial coloration by thermochromism.

The aliphatic ring formed by $R^7$ and $R^8$ is particularly preferably a nonsubstituted aliphatic hydrocarbon ring or an aliphatic hydrocarbon ring having at least one substituent selected from the group consisting of alkyl group, haloalkyl group, cycloalkyl group, alkoxy group, amino group, aralkyl group, aryl group and halogen atom. Examples of the alkyl group, haloalkyl group, cycloalkyl group, alkoxy group, amino group, aralkyl group, aryl group and halogen atom are the same as those enumerated for $R^3$ and $R^4$.

More preferred examples include mono-rings such as cyclohexane ring, cyclooctane ring and cycloheptane ring, bicyclo rings such as norbornane ring and bicyclononane ring, tricyclo rings such as adamantane ring, and rings obtained by substituting any one of these rings by at least one lower alkyl group having 4 or less carbon atoms such as methyl group. Out of these, mono-rings produce a particularly excellent effect from the viewpoint of reducing initial coloration by thermochromism while retaining high double peak characteristic and a high fading speed.

In the present invention, most preferred typical examples of the mono-ring formed by bonding together $R^7$ and $R^8$ are represented by the following formulas. In the following formulas, the carbon atom denoted by 13 is the 13-position carbon atom.

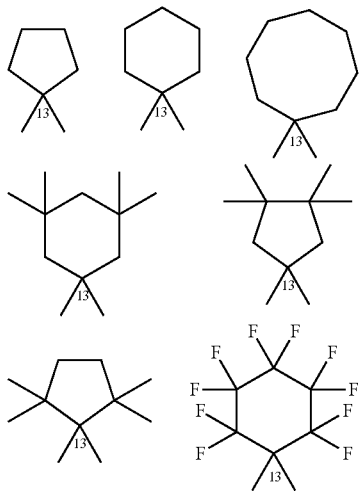

Out of the above mono-rings, a cyclooctane ring and a 3,3,5,5-tetramethylcyclohexane ring are most preferred.

<Particularly Preferred Chromene Compound>

Out of the chromene compounds of the present invention, a chromene compound of the above formula (1) in which $R^1$ and $R^2$ are the combination (i), that is, both $R^1$ and $R^2$ are each independently a group selected from thiol group, alkylthio group, alkoxyalkylthio group, haloalkylthio group, cycloalkylthio group, arylthio group and heteroarylthio group is particularly preferred from the viewpoint of high double peak characteristic and high color optical density. For the same reason, chromene compounds represented by the following formulas (5) and (6) are also particularly preferred.

That is, a chromene compound represented by the following formula (5) is preferred.

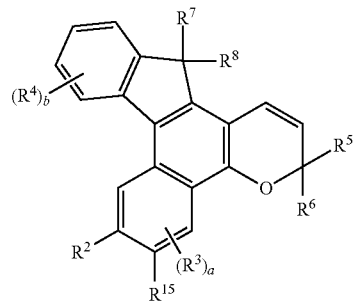

(5)

In the above formula, $R^3$, $R^4$, $R^5$, $R^6$, $R^7$, $R^8$, "a" and "b" are as defined in the above formula (2), $R^2$ is the same as $R^2$ of the combination (iii) in the above formula (1), that is thiol group, alkylthio group, alkoxyalkylthio group, haloalkylthio group, cycloalkylthio group, arylthio group or heteroarylthio group, and $R^{15}$ is an electron donor group having a Hammett constant $\sigma_p$ of $-0.50$ to $-0.01$ out of the groups defined as $R^1$ of the combination (iii) in the above formula (1).

A chromene compound represented by the following formula (6) is also preferred.

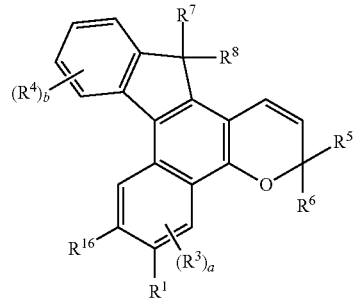

(6)

In the above formula, $R^3$, $R^4$, $R^5$, $R^6$, $R^7$, $R^8$, "a" and "b" are as defined in the above formula (2).

$R^1$ is the same as $R^1$ of the combination (ii) in the above formula (1), that is, thiol group, alkylthio group, alkoxyalkylthio group, haloalkylthio group, cycloalkylthio group, arylthio group or heteroarylthio group, and $R^{16}$ is an electron donor group having a Hammett constant $\sigma_p$ of $-0.50$ to $-0.01$ out of the groups defined as $R^2$ of the combination (ii) in the above formula (1).

$R^3$, $R^4$, $R^5$, $R^6$, $R^7$, $R^8$, "a" and "b" in the above formulas (5) and (6) are as defined in the above formula (2). As a matter of course, preferred examples of these groups are the same as those enumerated in the above formula (2).

$R^2$ in the above formula (5) and $R^1$ in the above formula (6) are each independently a thiol group, alkylthio group, alkoxyalkylthio group, haloalkylthio group, cycloalkylthio group, arylthio group or heteroarylthio group. Examples of these groups are the same as those enumerated for the above sulfur-containing substituent. As a matter of course, preferred examples of these are the same as those enumerated for the above sulfur-containing substituent.

$R^{15}$ in the above formula (5) and $R^{16}$ in the above formula (6) are electron donor groups having a Hammett constant $\sigma_p$ of $-0.50$ to $-0.01$ out of the groups defined as $R^1$ of the combination (iii) in the above formula (1) and out of the groups defined as $R^2$ of the combination (ii) in the above formula (1), respectively. When both $R^{15}$ and $R^{16}$ are the above electron donor groups, an excellent effect is obtained.

The Hammett constant $\sigma_p$ is defined based on the Hammett equation that quantifies the electric effect of a substituent bonded to an π electron system on the basis of the dissociation constant Ka of p-substituted benzoic acid. A substituent having a Hammett constant $\sigma_p$ of 0 is a hydrogen atom.

$R^{15}$ in the above formula (5) and $R^{16}$ in the above formula (6) are particularly preferably electron donor groups having a $\sigma_p$ of $-0.50$ to $-0.01$. When the chromene compound has an electron donor group which satisfies this range, its double peak characteristic can be intensified while initial coloration is suppressed.

Examples of the electron donor group having a $\sigma_p$ of $-0.50$ to $-0.01$ and represented by $R^{15}$ include aliphatic heterocyclic groups having a ring member nitrogen atom and bonded to the benzene ring to which the aliphatic heterocyclic group bonds via the nitrogen atom such as morpholino group ($\sigma_p=-0.50$), alkoxy groups such as methoxy group ($\sigma_p=-0.28$), ethoxy group ($\sigma_p=-0.21$) and propoxy group ($\sigma_p=-0.26$), alkyl groups such as methyl group ($\sigma_p=-0.14$), ethyl group ($\sigma_p=-0.13$) and propyl group ($\sigma_p=-0.12$), and cycloalkyl groups such as cyclohexyl group ($\sigma_p=-0.16$).

Examples of the electron donor group having a $\sigma_p$ of $-0.50$ to $-0.01$ and represented by $R^{16}$ include heterocyclic groups having a ring member nitrogen atom and bonded to the benzene ring to which the heterocyclic group bonds via the nitrogen atom such as morpholino group ($\sigma_p=-0.50$), alkoxy groups such as methoxy group ($\sigma_p=-0.28$), ethoxy group ($\sigma_p=-0.21$) and propoxy group ($\sigma_p=-0.26$), p-alkylaminophenyl groups such as p-dimethylaminophenyl group ($\sigma_p=-0.22$) and p-diethylaminophenyl group ($\sigma_p=-0.22$), alkoxyphenyl groups such as p-methoxyphenyl group ($\sigma_p=-0.04$) and o,p-dimethoxyphenyl group ($\sigma_p=-0.08$), aryl groups such as phenyl group ($\sigma_p=-0.01$), 1-naphthyl group ($\sigma_p=-0.08$) and 2-naphthyl group ($\sigma_p=-0.02$), p-nitrogen atom-containing heterocyclic aryl groups such as p-morpholinophenyl group ($\sigma_p=-0.16$), alkyl groups such as methyl group ($\sigma_p=-0.14$), ethyl group ($\sigma_p=-0.13$) and propyl group ($\sigma_p=-0.12$), and cycloalkyl groups such as cyclohexyl group ($\sigma_p=-0.16$).

Out of these, groups having a $\sigma_p$ of $-0.50$ to $-0.02$ are more preferred, groups having a $\sigma_p$ of $-0.50$ to $-0.10$ are much more preferred, and groups having a $\sigma_p$ of $-0.50$ to $-0.20$ are particularly preferred because balance between initial coloration and double peak characteristic becomes excellent. Particularly preferred examples of the group include alkoxy groups such as methoxy group and ethoxy group, and aliphatic heterocyclic groups having a ring member nitrogen atom and bonded to the benzene ring to which the aliphatic heterocyclic groups bond via the nitrogen atom such as morpholino group from the above point of view.

Particularly preferred examples of the chromene compound in the present invention are given below.

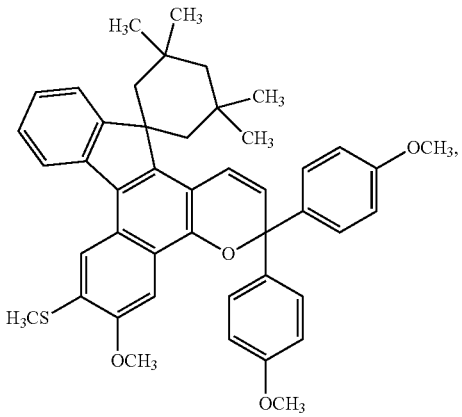

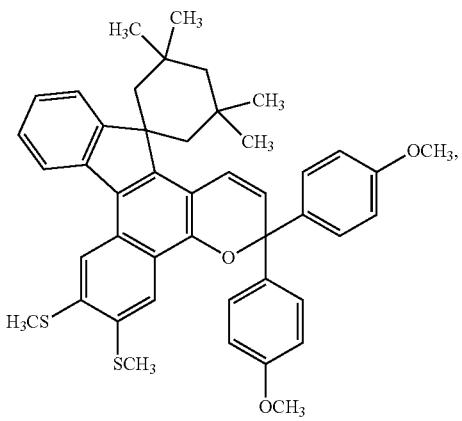

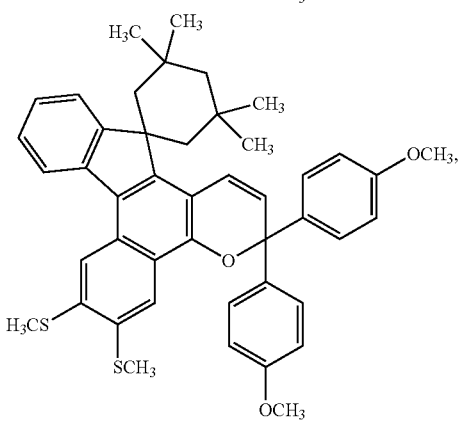

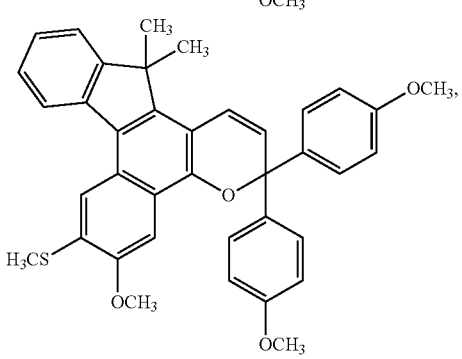

-continued

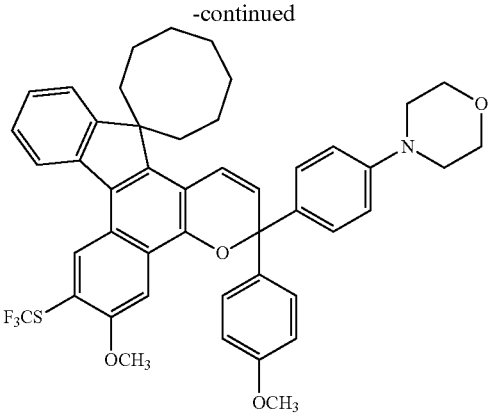

(Identification of Chromene Compound)

The chromene compound of the present invention is generally existent as an achromatic, light yellow or light green solid or viscous liquid at normal temperature and normal pressure and can be confirmed by the following means (1) to (3).

(1) When the proton nuclear magnetic resonance spectrum ($^1$H-NMR) of the chromene compound is measured, peaks based on an aromatic proton and an alkene proton appear at δ of around 5.0 to 9.0 ppm and peaks based on the protons of an alkyl group and an alkylene group appear at δ of around 1.0 to 4.0 ppm. By comparing these spectral intensities relatively, the number of the protons of bonds can be known.
(2) The composition of a corresponding product can be determined by elemental analysis.
(3) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of alkene and alkine appear at δ of around 80 to 140 ppm, and peaks based on the carbons of an alkyl group and an alkylene group appear at δ of around 20 to 80 ppm.

<Production of Chromene Compound>

The production process of the chromene compound of the present invention is not particularly limited, and any synthesis process may be employed. The chromene compound represented by the above formula (1) can be advantageously produced, for example, by the following process.

That is, the chromene compound can be advantageously produced by reacting a naphthol compound represented by the following formula (7) with a propargyl alcohol compound represented by the following formula (8) in the presence of an acid catalyst.

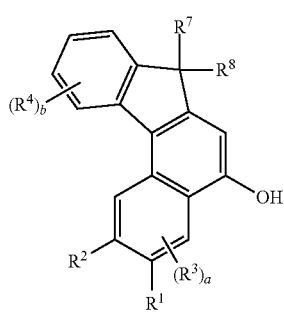

(7)

(wherein $R^1$, $R^2$, $R^3$, $R^4$, $R^7$, $R^8$, "a" and "b" are as defined in the above formula (2).)

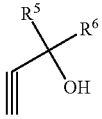

(8)

(wherein $R^5$ and $R^6$ are as defined in the above formula (2).)

The reaction ratio of the naphthol compound to the propargyl alcohol compound is selected from a wide range, generally 1:10 to 10:1 (molar ratio). As the acid catalyst is used sulfuric acid, benzenesulfonic acid, p-toluenesulfonic acid or acid alumina. The acid catalyst is used in an amount of 0.1 to 10 parts by weight based on 100 parts by weight of the total of the naphthol compound and the propargyl alcohol compound. The reaction temperature is preferably 0 to 200° C., and an aprotic organic solvent such as N-methylpyrrolidone, dimethyl formamide, tetrahydrofuran, benzene or toluene is preferably used as the solvent. The method of purifying the product obtained through the above reaction is not particularly limited. For example, the obtained product may be purified by carrying out silica gel column purification and further recrystallization.

The naphthol compound represented by the above formula (7) is provided as a novel compound by the present invention. In the formula (7), the definitions of $R^1$, $R^2$, $R^3$, $R^4$, $R^7$, $R^8$, "a" and "b" are the same as in the above formula (2). Therefore, it should be understood that the above explanation of the formula (2) is directly applied to these groups and parts.

In the present invention, preferred examples of the naphthol compound represented by the formula (7) are the following compounds.

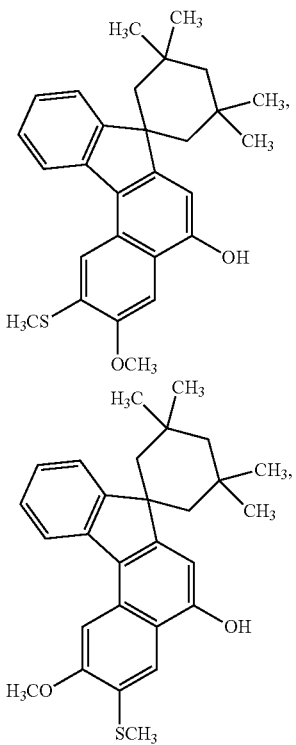

($R^1$, $R^2$, $R^3$ and "a" are as defined in the above formula (2).)

For example, benzene compounds represented by the following formulas (10a) and (10b) can be purchased as commercially available products.

(10a)

(10b)

For example, a benzene compound represented by the following formula (11) can be synthesized in accordance with a reaction method described in research papers such as Organometallics. 8. (5). 1303-1308; 1989.

(11)

A compound represented by the following formula (12) is obtained by reacting the compound (9) with acid chloride ($R^4$ and "b" are as defined in the above formula (2)).

(12)

To determine the positions of substituents of $R^1$ and $R^2$ in the obtained naphthol compound of the formula (7), a benzene compound of the formula (9) prepared by adjusting the types and degrees of electron donating ability of the substituent groups is preferably used. For example, to synthesize a naphthol compound in which $R^1$ and $R^2$ are the same electron donor groups (for example, the same sulfur-containing substituents), the benzene compound of the formula (11) is preferably used.

To synthesize a naphthol compound in which $R^1$ is a substituent having higher electron donating ability than $R^2$, the benzene compound of the formula (10a) is preferably used.

Further, to synthesize a naphthol compound in which $R^1$ is a substituent having lower electron donating ability than $R^2$, a compound represented by the formula (12) is first produced by using the benzene compound of the above formula (10a). Then, in the subsequent step after the production of the compound of the formula (12), a chlorine atom should be converted into desired $R^2$ by using a Buchwald-Hartwig cross-coupling reaction.

Ordinary naphthol compounds can be synthesized in accordance with reaction methods described in, for example, research papers such as Journal of Organic Chemistry 69(10) 3282-3293; 2004, Synthetic Communications 23(16) 2241-2249 (1993) and WO01/60881.

(Process of Synthesizing Naphthol Compound)

Although the process of synthesizing the naphthol compound represented by the above formula (7) is not particularly limited, it can be synthesized as follows, for example.

A benzene compound represented by the following formula (9) may be purchased as a commercially available product or may be synthesized based on the following documents.

(9)

A compound represented by the following formula (13) is obtained by carrying out the Stobbe reaction and cyclization reaction of the above compound (12).

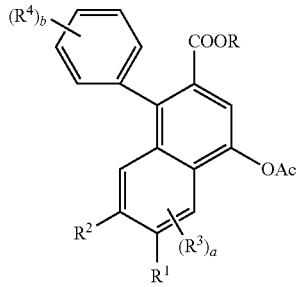

(13)

In the compound of the formula (13), R is a group derived from a diester compound used in the Stobbe reaction. The compound (13) is then hydrolyzed by using an alkali or acid to obtain a carboxylic acid represented by the following formula (14).

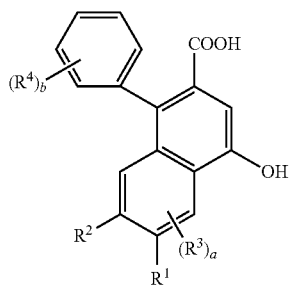

(14)

This carboxylic acid is benzylated by using a base such as potassium carbonate and benzyl chloride and then hydrolyzed by using an alkali or acid to obtain a benzyl-protected carboxylic acid represented by the following formula (15).

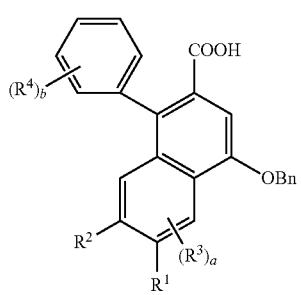

(15)

This benzyl-protected carboxylic acid is converted into an amine by a method such as Curtius rearrangement, Hofmann rearrangement or Lossen rearrangement, and a diazonium salt is prepared from the amine. This diazonium salt is converted into a bromide through a Sandmeyer reaction or the like, and the obtained bromide is reacted with magnesium or lithium to prepare an organic metal reagent. This organic metal reagent is reacted with a ketone represented by the following formula (16) at −10 to 70° C. in an organic solvent for 10 minutes to 4 hours to obtain a compound represented by the following formula (17).

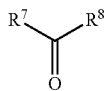

(16)

($R^7$ and $R^8$ are as defined in the above formula (2).)

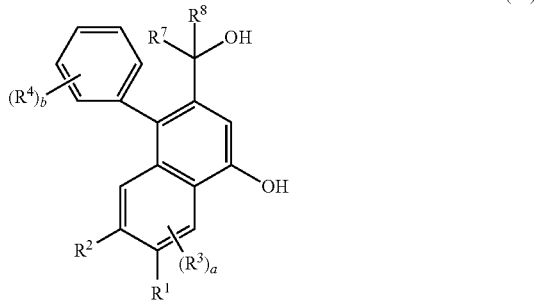

(17)

The compound (17) is reacted at 10 to 120° C. for 10 minutes to 2 hours under a neutral to acid condition to spironate the alcohol so as to obtain a naphthol compound of the above formula (7) of interest. In the above reaction, the reaction ratio of the above organic metal reagent to the ketone represented by the above formula (16) is selected from among a wide range but preferably selected from a range of 1:10 to 10:1 (molar ratio). The reaction temperature is preferably −10 to 70° C., and an aprotic organic solvent such as diethyl ether, tetrahydrofuran, benzene or toluene is preferably used as the solvent. The spironation of the alcohol material under a neutral to acid condition is preferably carried out by using an acid catalyst such as acetic acid, hydrochloric acid, sulfuric acid, benzenesulfonic acid, p-toluenesulfonic acid or acid alumina. The acid catalyst is preferably used in an amount of 0.1 to 10 parts by weight based on 100 parts by weight of the alcohol material. For this spironation, a solvent such as tetrahydrofuran, benzene or toluene is used.

The propargyl alcohol compound represented by the above formula (8) can be synthesized by various methods. For example, it can be easily synthesized by reacting a ketone compound corresponding to the above formula (8) with a metal acetylene compound such as lithium acetylide.

The chromene compound of the present invention which is synthesized as described above dissolves well in a general-purpose organic solvent such as toluene, chloroform or tetrahydrofuran. When the chromene compound represented by the above formula (1) is dissolved in this solvent, the obtained solution is generally almost achromatic and transparent and has an excellent photochromic function that it develops a color swiftly upon exposure to sunlight or ultraviolet radiation and reversibly returns to its original achromatic state swiftly by blocking off the light.

(Combination with Another Photochromic Compound>

Although the chromene compound of the present invention develops a color of a neutral tint by itself, it may be used in combination with another photochromic compound to obtain various colors required as a photochromic lens. Any known compound may be used as the photochromic compound to be combined with. Examples of the photochromic compound include fulgide, fulgimide, spirooxazine and chromene. Out of these, a chromene compound is particularly preferred because it can keep a color uniformly at the time of color development and fading, can suppress a color shift at the time of color development due to the deterioration of photochromic properties and further can reduce initial coloration.

That is, by combining the chromene compound of the present invention with another chromene compound which has high color development sensitivity, a high fading speed and little initial coloration like the above chromene compound, a photochromic composition which keeps a color uniformly at the time of color development and fading and provides high transparency can be obtained.

To provide high transparency, the chromene compound to be combined with preferably has a transmittance by thermochromism of not less than 75% and an absorption end of an ultraviolet absorption curve at 380 to 430 nm. Further, a chromene compound having a transmittance by thermochromism of not less than 85% and an absorption end of an ultraviolet absorption curve at 380 to 420 nm is particularly preferred, and a chromene compound having a transmittance by thermochromism of not less than 88% and an absorption end of an ultraviolet absorption curve at 380 to 410 nm is most preferred. The transmittance by thermochromism and the absorption end of the ultraviolet absorption curve are values measured by methods described in the following examples.

These preferred chromene compounds to be combined with include chromene compounds represented by the following formulas (18a) and (18b).

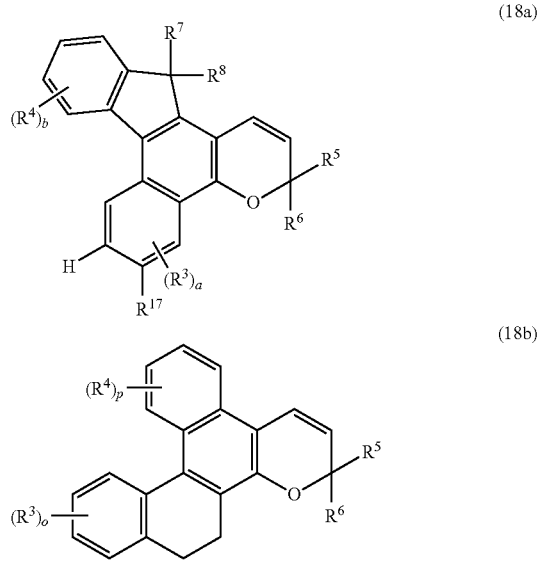

In the above formula (18a), $R^3$, $R^4$, $R^5$, $R^6$, $R^7$ and $R^8$ are as defined in the above formula (2), and $R^{17}$ is a hydrogen atom, hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. Specific examples of the chromene compound of the above formula (18a) are the same as compounds enumerated in a pamphlet of International Laid-Open WO2001/60811.

In the above formula (18b), $R^3$, $R^4$, $R^5$ and $R^6$ are as defined in the above formula (2), and "o" and "p" are each independently an integer of 0 to 4. Specific examples of the chromene compound of the above formula (18b) are the same as compounds enumerated in a pamphlet of International Laid-Open WO2009/136668.

To obtain a photochromic composition comprising the chromene compound of the present invention and another photochromic compound, the ratio of these chromene compounds may be suitably determined according to a desired color. In this case, the amount of the chromene compound of the present invention or another chromene compound is preferably 0.001 to 10 parts by mass based on 100 parts by mass of the total of all the polymerizable monomers. Stated more specifically, in the case of a thin film such as a coating film (for example, a thin film having a thickness of about 100 μm), the color should be controlled by using 0.001 to 5.0 parts by mass of the chromene compound of the present invention and 0.001 to 5.0 parts by mass of another chromene compound based on 100 parts by mass of the coating film or all of the polymerizable monomers which provide the coating film. In the case of a thick cured material (having a thickness of 1 mm or more, for example), the color should be controlled by using 0.001 to 0.5 part by mass of the chromene compound of the present invention and 0.001 to 0.5 part by mass of another chromene compound based on 100 parts by mass of the thick cured material or all of the polymerizable monomers which provide the thick cured material.

(Stabilizer to be Combined with)

Although the chromene compound of the present invention has high durability as it is, its durability can be further enhanced by using the following ultraviolet absorbent, optical stabilizer or antioxidant. As the ultraviolet absorbent may be used known ultraviolet absorbents such as benzophenone-based compounds, benzotriazole-based compounds, cyanoacrylate compounds, triazine-based compounds and benzoate-based compounds. Cyanoacrylate-based compounds and benzophenone-based compounds are particularly preferred. When the above ultraviolet stabilizer is used in an amount of 0.001 to 5 parts by mass based on 100 parts by mass of the total of all the polymerizable monomers including the chromene compound of the present invention, it produces an effect. Known hindered amines may be used as the optical stabilizer, and known hindered phenols may be used as the antioxidant. When the above optical stabilizer and antioxidant are each used in an amount of 0.01 to 10 parts by mass based on 100 parts by mass of the total of all the polymerizable monomers including the chromene compound of the present invention, they produce an effect.

(Use of Chromene Compound>

The chromene compound of the present invention exhibits the same photochromic properties even in a polymer solid matrix. The polymer solid matrix is not particularly limited if the chromene compound of the present invention can be uniformly dispersed therein. Optically preferred examples of the polymer solid matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane and polycarbonates.

Thermosetting resins obtained by polymerizing a radically polymerizable polyfunctional monomer may be used as the above polymer matrix. Examples of the radically polymerizable polyfunctional monomer include polyacrylic acid and polymethacrylic acid ester compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane and 2,2-bis(3,5-dibromo-4-methacryloyloxyethoxyphenyl)propan e; polyallyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate and trimethylolpropane triallyl carbonate; polythioacrylic acid and polythiomethacrylic acid ester compounds such as 1,2-bis(methacryloylthio)ethane, bis(2-acryloylthioethyl)ether and 1,4-bis(methacryloylthiomethyl)benzene; acrylic acid ester compounds and methacrylic acid ester compounds such as glycidyl acrylate, glycidyl methacrylate, β-methyl glycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate; and divinylbenzene.

Copolymers obtained by copolymerizing the above radically polymerizable polyfunctional monomer with a radically polymerizable monofunctional monomer may also be used as the above polymer matrix. Examples of the radically polymerizable monofunctional monomer include unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate and 2-hydroxyethyl methacrylate; fumaric acid ester compounds such as diethyl fumarate and diphenyl fumarate; thioacrylic acid and thiomethacrylic acid ester compounds such as methyl thioacrylate, benzyl thioacrylate and benzyl thiomethacrylate; and vinyl compounds such as styrene, chlorostyrene, methylstyrene, vinyl naphthalene, α-methylstyrene dimer and bromostyrene.

Commonly used methods may be employed to disperse the chromene compound of the present invention into the above polymer solid matrix. The methods include one in which the above thermoplastic resin and the chromene compound are kneaded together while they are molten to disperse the chromene compound into the resin, one in which the chromene compound is dissolved in the above polymerizable monomers and a polymerization catalyst is added to the resulting solution to polymerize the polymerizable monomers by heat or light so as to disperse the chromene compound into the resin, and one in which the surfaces of the above thermoplastic resin and the above thermosetting resin are dyed with the chromene compound to disperse the chromene compound into the resins.

The chromene compound of the present invention can be used as a photochromic material in a wide range of fields such as recording materials as substitutes for silver halide photosensitive materials, copy materials, printing photosensitive materials, recording materials for cathode ray tubes, photosensitive materials for lasers and photosensitive materials for holography. The photochromic material comprising the chromene compound of the present invention may be used as a photochromic plastic lens material, optical filter material, display material, actinometer or ornament material.

For instance, when the chromene compound of the present invention is used in a photochromic plastic lens, if uniform light control performance is obtained, the lens manufacturing method is not particularly limited. Examples of the method include one in which a polymer film containing the photochromic material of the present invention uniformly dispersed therein is sandwiched between lenses, one in which the chromene compound of the present invention is dispersed into the above polymerizable monomers and the polymerizable monomers are polymerized by a predetermined technique, and one in which the chromene compound is dissolved in silicone oil, the resulting solution is impregnated into the surface of a lens at 150 to 200° C. for 10 to 60 minutes, and the surface is further coated with a curable substance to obtain a photochromic lens. Further, one in which the above polymer film is formed on the surface of the lens and the surface is coated with a curable substance to obtain a photochromic lens is also employed.

A coating agent composed of a polymerization curable composition comprising the chromene compound of the present invention may be applied to the surface of a lens substrate, and the coating film may be cured. At this point, the lens substrate may be subjected to a surface treatment with an alkaline solution or a plasma treatment in advance, and a primer may be further applied to improve adhesion between the substrate and the coating film by carrying out the above surface treatment or without the surface treatment.

EXAMPLES

The following examples are provided for the purpose of further illustrating the present invention but are in no way to be taken as limiting.

Example 1

1.0 g (2.3 mmol) of the following naphthol compound (19) and 0.80 g (3.0 mmol) of the following propargyl alcohol compound (20) were dissolved in 70 ml of toluene, and 0.022 g of p-toluenesulfonic acid was further added to the resulting solution and stirred under heating and reflux for 1 hour. After the reaction, the solvent was removed, and the obtained product was purified on silica gel by chromatography to obtain 1.2 g of a white powder product. The yield rate was 76%.

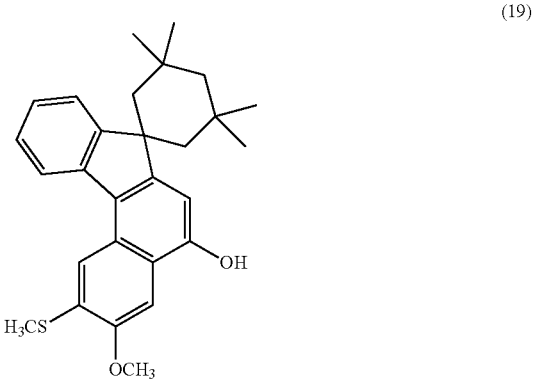

(19)

(20)

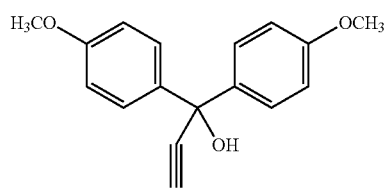

(21)

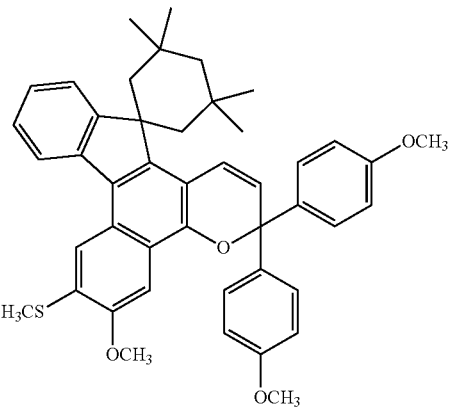

The elemental analysis values of this product were 79.21% of C, 6.89% of H and 4.61% of S which were almost equal to the calculated values of $C_{45}H_{46}O_4S$ (C, 79.14%; H, 6.79%; S, 4.70%).

When the proton nuclear magnetic resonance spectrum of the product was measured, 18H peaks based on the methyl and methylene protons of a tetramethylcyclohexane ring were seen at δ of around 1.0 to 3.0 ppm, 12H peaks based on the methyl protons of a methylthio group and a methoxy group were seen at δ of around 2.3 to 4.0 ppm, and 16H peak based on an aromatic proton and an alkene proton were seen at δ of around 5.6 to 9.0 ppm.

Further, when the $^{13}C$-nuclear magnetic resonance spectrum of the product was measured, a peak based on the carbon of an aromatic ring was seen at δ of around 110 to 160 ppm, a peak based on the carbon of an alkene was seen at δ of around 80 to 140 ppm, and a peak based on the carbon of an alkyl was seen at δ of 20 to 60 ppm.

It was confirmed from the above results that the isolated product was a compound represented by the following formula (21).

Examples 2 to 5

Chromene compounds shown in Table 1 (Examples 2 and 3) and Table 2 (Examples 4 and 5) were synthesized in the same manner as in Example 1. When the structures of the obtained products were analyzed by using the same structure checking means as in Example 1, it was confirmed that they were compounds represented by structural formulas shown in Table 1 and Table 2. The elemental analysis values of these compounds, the calculated values obtained from the structural formulas of the compounds and characteristic $^1H$-NMR spectra are shown in Table 3.

TABLE 1

| Example No. | Naphthol compound | Propargyl alcohol compound | Product | Yield rate |
|---|---|---|---|---|
| 2 | | | | 79 |
| 3 | | | | 71 |

TABLE 2

| Example No. | Raw materials | | Product | Yield rate |
|---|---|---|---|---|
| | Naphthol compound | Propargyl alcohol compound | | |
| 4 | [structure] | [structure] | [structure] | 83 |
| 5 | [structure] | [structure] | [structure] | 76 |

TABLE 3

| Example No. | Experimental values | | | | Calculated values | | | | 1H-NMR (ppm) |
|---|---|---|---|---|---|---|---|---|---|
| | C | H | N | S | C | H | N | S | |
| 2 | 79.22 | 6.90 | 0.00 | 4.76 | 79.14 | 6.79 | 0.00 | 4.70 | δ5.0-9.0 16H  δ0.5-4.5 30H |
| 3 | 77.21 | 6.60 | 0.00 | 9.09 | 77.33 | 6.63 | 0.00 | 9.17 | δ5.0-9.0 16H  δ0.5-4.5 30H |
| 4 | 77.74 | 5.77 | 0.00 | 5.42 | 77.79 | 5.84 | 0.00 | 5.47 | δ5.0-9.0 16H  δ0.5-4.5 18H |
| 5 | 72.22 | 5.95 | 1.69 | 4.11 | 72.33 | 5.81 | 1.83 | 4.20 | δ5.0-9.0 16H  δ0.5-4.5 28H |

Examples 6 to 10

(Evaluation of Physical Properties of Photochromic Plastic Lens Produced by Coating Method)

The chromene compound No. 1 obtained in the above Example 1 was mixed with a photopolymerization initiator and polymerizable monomers, the resulting mixture was applied to the surface of a lens substrate, and ultraviolet light was applied to polymerize the coating film on the surface of the lens substrate.

As for a photochromic curable composition, a mixture of 50 parts by mass of 2,2-bis(4-methacryloyloxypentaethoxyphenyl)propane, 10 parts by mass of polyethylene glycol diacrylate (average molecular weight of 532), 10 parts by mass of trimethylolpropane trimethacrylate, 10 parts by mass of polyester oligomer hexaacrylate (EB-1830 of Daicel UCB Co., Ltd.) and 10 parts by mass of glycidyl methacrylate as radically polymerizable monomers was used. 1 part by mass of the chromene compound No. 1 obtained in Example 1 was added to and fully mixed with 90 parts by mass of this mixture of the radical polymerizable monomers, and 0.3 part by mass of CGI1800 {a mixture of 1-hydroxycyclohexylphenyl ketone and bis(2,6-dimethoxybenzoyl)-2,4,4-trimethyl-pentyl phosphine oxide (weight ratio of 3:1)} as a photopolymerization initiator, 5 parts by mass of bis(1,2,2,6,6-pentamethyl-4-piperidyl)sebacate as a stabilizer, 3 parts by mass of ethylenebis(oxyethylene)bis[3-(5-tert-butyl-4-hydroxy-m-tolyl)propionate], 7 parts by mass of γ-methacryloyloxypropyl trimethoxysilane as a silane coupling agent and 3 parts by mass of N-methyldiethanolamine were added to and fully mixed with the above mixture to obtain a photochromic curable composition.

Subsequently, about 2 g of the photochromic curable composition obtained by the above method was applied to the surface of a lens substrate (CR39: acrylic resin plastic lens; refractive index of 1.50) by using the 1H-DX2 spin coater of MIKASA Co., Ltd. This coated lens was irradiated with light of a metal halide lamp having an output of 120 mW/cm² in a nitrogen gas atmosphere for 3 minutes to cure the photochromic curable composition so as to produce an optical article coated with a cured polymer film containing the chromene compound dispersed therein (thickness of polymer film: 40 µm) (photochromic plastic lens).

The following photochromic properties of the obtained photochromic plastic lenses were evaluated. The evaluation results of the photochromic plastic lenses comprising the chromene compound of Example 1 are shown in Table 4.

[1] Maximum absorption wavelength (λmax): This is the maximum absorption wavelength after color development obtained by means of the spectrophotometer (MCPD3000 instantaneous multi-channel photodetector) of Otsuka Electronics Co., Ltd. and used as an index of color at the time of color development.

[2] Color optical density ($A_0$): This is the difference between absorbance {$\epsilon(120)$ after 120 seconds of exposure and $\epsilon(0)$ under no exposure at the above maximum absorption wavelength and used as an index of color optical density. It can be said that as this value becomes larger, the photochromic properties become better.

[3] Double peak characteristic ($A_Y/A_B$): This is the ratio of color optical density ($A_Y$: value of $\lambda_{max}$) at a yellow range (having a maximum absorption wavelength at 430 to 530 nm) and color optical density ($A_B$: value of $\lambda_{max}$) at a blue range (having a maximum absorption wavelength at 550 to 650 nm) and used as an index of double peak characteristic.

[4] Fading half period [τ½ (sec.)]: time required for the reduction of the absorbance at the above maximum absorption wavelength of a sample to ½ of {$\epsilon(120)-\epsilon(0)$} when exposure is stopped after 120 seconds of exposure and used as an index of fading speed. As this time becomes shorter, the fading speed becomes higher.

[5] Absorption end {$\lambda_0$}: After the photochromic plastic lens obtained under the above conditions is used as a sample and kept in the dark for one day, the ultraviolet transmittance (T %) at 300 to 800 nm of the sample is measured with an ultraviolet visible spectrophotometer (UV-2550 of Shimadzu Corporation) at room temperature. A tangent line is drawn on the obtained ultraviolet absorption curve to ensure that the transmittance (T %) of the ultraviolet absorption curve passes a point of 50% so as to obtain an absorption wavelength at which the transmittance (T %) of the tangent line becomes 0 as the absorption end (absorption end of the ultraviolet spectrum) and used as an index of initial coloration. For example, in an optical article such as a spectacle lens, as this value becomes smaller, the initial coloration becomes weaker and the transparency under no exposure becomes higher.

[6] Thermochromism {$T_0$}: The photochromic plastic lens obtained under the above conditions is used as a sample and its transmittance (T %) at 300 to 800 nm is measured with an ultraviolet visible spectrophotometer (UV-2550 of Shimadzu Corporation) at room temperature. This is a transmittance at a wavelength at which the transmittance at 430 to 650 nm becomes minimal and used as an index of initial coloration. As this value becomes larger, the initial coloration becomes weaker and the transparency under no exposure becomes higher.

[7] Residual rate ($A_{50}/A_0\times100$): The deterioration promotion test of the obtained photochromic plastic lens is carried out by using the X25 xenon weather meter of Suga Test Instruments Co., Ltd. for 50 hours. Thereafter, the above color optical density is evaluated before and after the test, the color optical density ($A_0$) before the test and the color optical density ($A_{50}$) after the test are measured, and the ratio ($A_{50}/A_0$) of these values is taken as residual rate and used as an index of color development durability. As the residual rate becomes higher, the color development durability becomes higher.

Photochromic plastic lenses were obtained and their characteristic properties were evaluated in the same manner as above except that the compounds (Nos. 2 to 5) obtained in Examples 2 to 5 were used as the chromene compound. The results are shown in Table 4.

TABLE 4

| Example No. | Compound No. | λmax (nm) | Color optical density $A_O$ | Double peak characteristic $A_Y/A_B$ | Fading half period τ½ (sec) | Initial coloration (absorption end) (nm) | Initial coloration (thermochromism) (%) | Residual rate ($A_{50}/A_O$) × 100 (%) |
|---|---|---|---|---|---|---|---|---|
| 6 | 1 | 464 | 0.51 | 1.50 | 50 | 411 | 89 | 82 |
|   |   | 573 | 0.34 |      | 50 |     | 90 | 82 |
| 7 | 2 | 472 | 0.54 | 1.48 | 51 | 397 | 86 | 86 |
|   |   | 579 | 0.36 |      | 51 |     | 85 | 86 |
| 8 | 3 | 466 | 0.58 | 1.44 | 52 | 404 | 89 | 84 |
|   |   | 576 | 0.40 |      | 52 |     | 90 | 84 |
| 9 | 4 | 466 | 0.82 | 1.50 | 121 | 411 | 89 | 87 |
|   |   | 575 | 0.56 |      | 121 |     | 89 | 87 |
| 10 | 5 | 502 | 0.68 | 1.10 | 140 | 412 | 86 | 84 |
|    |   | 595 | 0.62 |      | 140 |     | 85 | 83 |

Comparative Examples 1 to 3

For comparison, photochromic plastic lenses were obtained and their physical properties were evaluated in the same manner as in Examples except that compounds represented by the following formulas (A), (B) and (C) were used. The results are shown in Table 5.

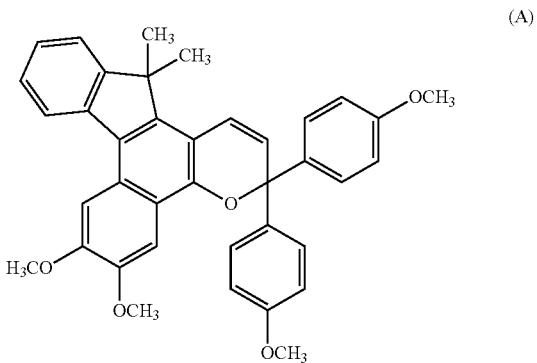

(A)

-continued

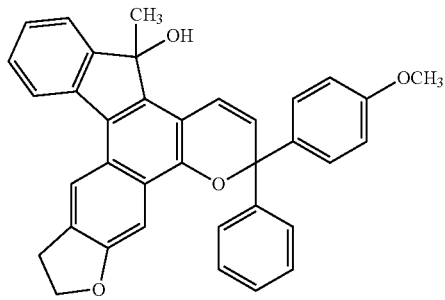

(B)

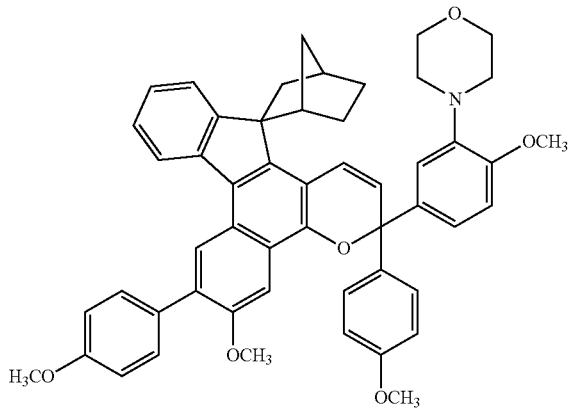

(C)

It is understood that the photochromic plastic lenses in Examples 6 to 10 which were obtained from the chromene compounds of the present invention are superior in all of color optical density, fading speed and durability to the photochromic plastic lenses of Comparative Example 1 (chromene compound represented by the above formula (A)), Comparative Example 2 (chromene compound of the above formula (B)) and Comparative Example 3 (chromene compound represented by the above formula (C)) while having high double peak characteristic.

The photochromic plastic lenses of Comparative Examples 1 and 2 have large initial coloration by thermochromism. The photochromic plastic lens of Comparative Example 3 has large initial coloration as the absorption end goes beyond 420 nm into a visible range. In contrast to this, in Examples in which the chromene compounds of the present invention are used, as thermochromism is little and the absorption end is existent at a short wavelength range, initial coloration is little.

Examples 11 to 49

Chromene compounds shown in Table 6 were synthesized in the same manner as in Example 1. When the structures of the obtained chromene compounds were analyzed in the same manner as in Example 1, it was confirmed that they were compounds represented by the structural formulas shown in Table 6. Table 7 shows the elemental analysis values and $^1$H-NMR spectral values of the chromene compounds obtained in Examples. In Table 7, the compound Nos. 11 to 49 are chromene compounds obtained in Examples 11 to 49, respectively.

TABLE 5

| Comparative Example No. | Compound No. | λmax (nm) | Color optical density $A_O$ | Double peak characteristic $A_Y/A_B$ | Fading half period $\tau^{1/2}$ (sec) | Initial coloration (absorption end) (nm) | Initial coloration (thermochromism) (%) | Residual rate $(A_{50}/A_O) \times 100$ (%) |
|---|---|---|---|---|---|---|---|---|
| 1 | (A) | 457 | 0.69 | 1.56 | 195 | 397 | 67 | 76 |
|   |     | 574 | 0.45 |      | 196 |     | 75 | 77 |
| 2 | (B) | 455 | 0.30 | 0.94 | 83  | 410 | 77 | 35 |
|   |     | 576 | 0.32 |      | 83  |     | 78 | 35 |
| 3 | (C) | 458 | 0.44 | 1.20 | 68  | 422 | 84 | 85 |
|   |     | 568 | 0.37 |      | 68  |     | 86 | 84 |

TABLE 6

| Example No. | Raw materials | | Product | Yield rate (%) |
|---|---|---|---|---|
| | Naphthol compound | Propargyl alcohol compound | | |
| 11 | | | | 76 |
| 12 | | | | 78 |
| 13 | | | | 72 |
| 14 | | | | 71 |

TABLE 6-continued
| Example No. | Raw materials | | Product | Yield rate (%) |
|---|---|---|---|---|
| | Naphthol compound | Propargyl alcohol compound | | |
| 15 | 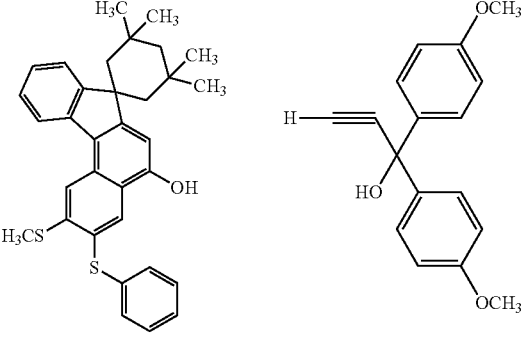 | 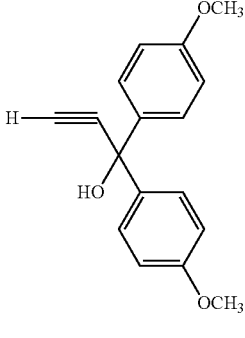 | 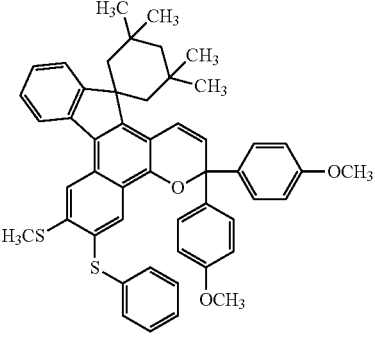 | 71 |
| 16 | 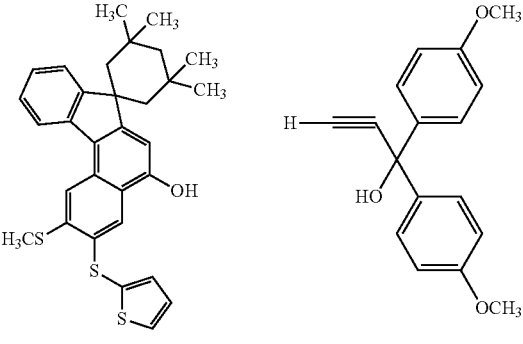 | 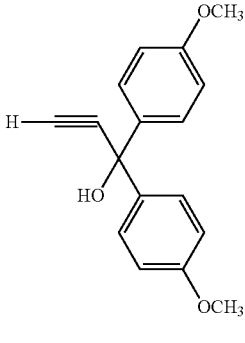 | 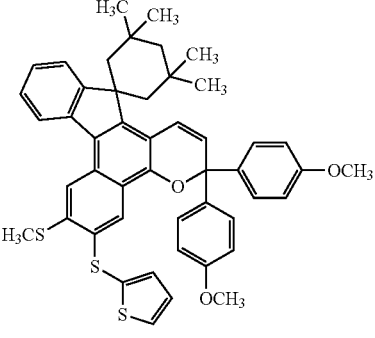 | 69 |
| 17 | 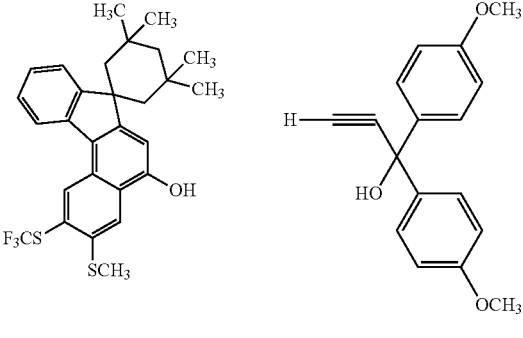 | 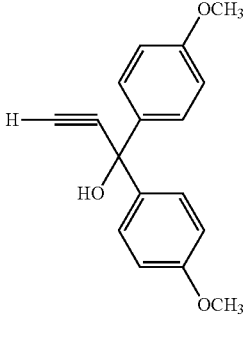 | 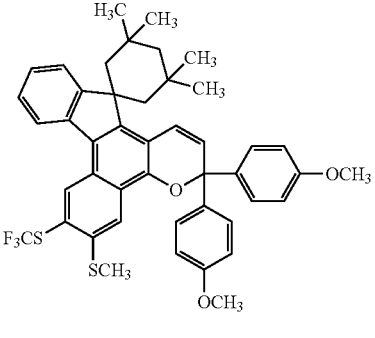 | 72 |
| 18 | 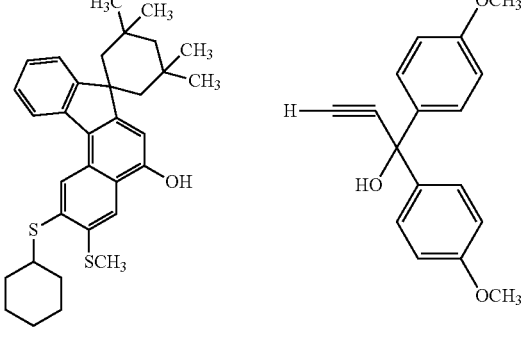 | 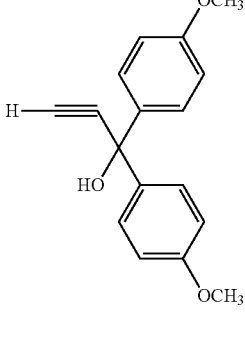 | 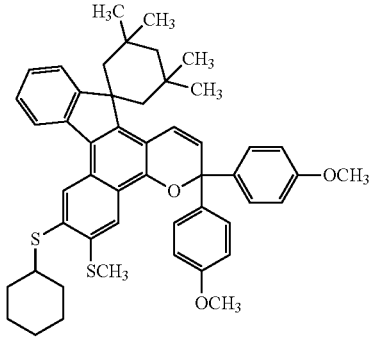 | 69 |

TABLE 6-continued

| Example No. | Raw materials | | Product | Yield rate (%) |
|---|---|---|---|---|
| | Naphthol compound | Propargyl alcohol compound | | |
| 19 | | | | 73 |
| 20 | | | | 70 |
| 21 | | | | 76 |
| 22 | | | | 72 |

TABLE 6-continued

| Example No. | Raw materials | | Product | Yield rate (%) |
| --- | --- | --- | --- | --- |
| | Naphthol compound | Propargyl alcohol compound | | |
| 23 | | | | 64 |
| 24 | | | | 69 |
| 25 | | | | 68 |
| 26 | | | | 66 |

TABLE 6-continued

| Example No. | Raw materials | | Product | Yield rate (%) |
|---|---|---|---|---|
| | Naphthol compound | Propargyl alcohol compound | | |
| 27 | | | | 75 |
| 28 | | | | 71 |
| 29 | | | | 60 |
| 30 | | | | 77 |

TABLE 6-continued

| Example No. | Raw materials | | Product | Yield rate (%) |
|---|---|---|---|---|
| | Naphthol compound | Propargyl alcohol compound | | |
| 31 | | | | 66 |
| 32 | | | | 71 |
| 33 | | | | 70 |
| 34 | | | | 69 |

TABLE 6-continued

| | Raw materials | | | |
|---|---|---|---|---|
| Example No. | Naphthol compound | Propargyl alcohol compound | Product | Yield rate (%) |
| 35 | | | | 69 |
| 36 | | | | 76 |
| 37 | | | | 69 |
| 38 | | | | 68 |

TABLE 6-continued

| Example No. | Raw materials | | Product | Yield rate (%) |
| --- | --- | --- | --- | --- |
| | Naphthol compound | Propargyl alcohol compound | | |
| 39 | | | | 66 |
| 40 | | | | 62 |
| 41 | | | | 69 |
| 42 | | | | 68 |

TABLE 6-continued

| Example No. | Raw materials | | Product | Yield rate (%) |
| --- | --- | --- | --- | --- |
| | Naphthol compound | Propargyl alcohol compound | | |
| 43 | | | | 68 |
| 44 | | | | 69 |
| 45 | | | | 71 |
| 46 | | | | 66 |

TABLE 6-continued
| Example No. | Raw materials | | Product | Yield rate (%) |
|---|---|---|---|---|
| | Naphthol compound | Propargyl alcohol compound | | |
| 47 | 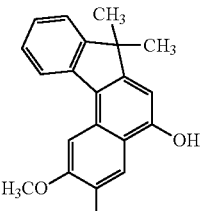 | 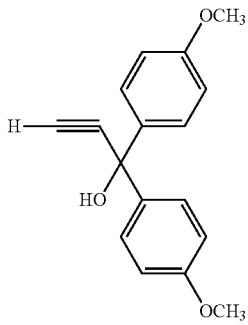 | 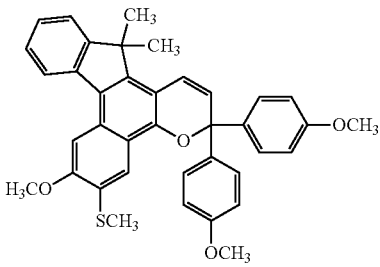 | 78 |
| 48 | 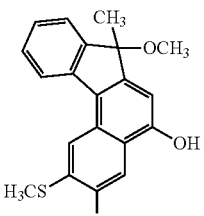 | 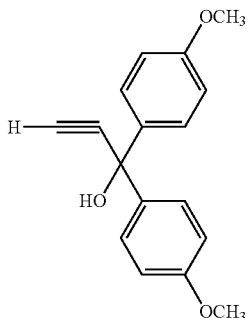 | 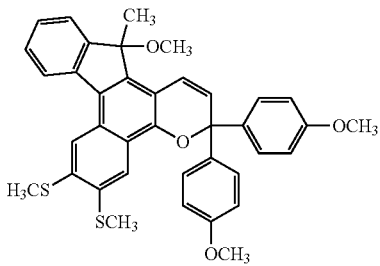 | 71 |
| 49 | 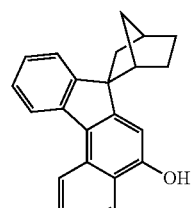 | 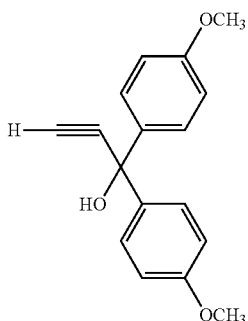 | 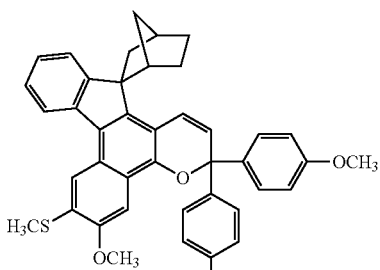 | 63 |
TABLE 7
| Compound No. | Elemental analysis values | | | | | | | | $^1$H-NMR (NMR) |
|---|---|---|---|---|---|---|---|---|---|
| | Experimental values | | | | Calculated values | | | | |
| | C | H | N | S | C | H | N | S | |
| 11 | 77.13 | 6.47 | 0 | 9.39 | 77.15 | 6.47 | 0 | 9.36 | δ5.0-9.0 16H δ0.5-4.5 28H |
| 12 | 75.78 | 6.65 | 0 | 8.82 | 75.79 | 6.64 | 0 | 8.8 | δ5.0-9.0 16H δ0.5-4.5 32H |
| 13 | 71.77 | 5.78 | 0 | 8.52 | 71.78 | 5.76 | 0 | 8.52 | δ5.0-9.0 16H δ0.5-4.5 27H |
| 14 | 78.27 | 7.13 | 0 | 8.34 | 78.29 | 7.1 | 0 | 8.36 | δ5.0-9.0 16H δ0.5-4.5 38H |
| 15 | 78.94 | 6.37 | 0 | 8.44 | 78.91 | 6.36 | 0 | 8.43 | δ5.0-9.0 21H δ0.5-4.5 27H |
| 16 | 75.18 | 6.06 | 0 | 12.54 | 75.16 | 6.04 | 0 | 12.54 | δ5.0-9.0 15H δ0.5-4.5 31H |
| 17 | 71.79 | 5.78 | 0 | 8.52 | 71.78 | 5.76 | 0 | 8.52 | δ5.0-9.0 16H δ0.5-4.5 27H |

TABLE 7-continued

| Compound No. | Experimental values | | | | Calculated values | | | | $^1$H-NMR (NMR) |
|---|---|---|---|---|---|---|---|---|---|
| | C | H | N | S | C | H | N | S | |
| 18 | 78.31 | 7.12 | 0 | 8.34 | 78.29 | 7.1 | 0 | 8.36 | δ5.0-9.0 16H |
| | | | | | | | | | δ0.5-4.5 38H |
| 19 | 77.16 | 6.44 | 0 | 9.38 | 77.15 | 6.47 | 0 | 9.36 | δ5.0-9.0 16H |
| | | | | | | | | | δ0.5-4.5 28H |
| 20 | 78.93 | 6.37 | 0 | 8.44 | 78.91 | 6.36 | 0 | 8.43 | δ5.0-9.0 21H |
| | | | | | | | | | δ0.5-4.5 27H |
| 21 | 81.05 | 6.94 | 0 | 4.82 | 81.04 | 6.95 | 0 | 4.81 | δ5.0-9.0 16H |
| | | | | | | | | | δ0.5-4.5 30H |
| 22 | 81.73 | 7.42 | 0 | 4.37 | 81.7 | 7.41 | 0 | 4.36 | δ5.0-9.0 16H |
| | | | | | | | | | δ0.5-4.5 38H |
| 23 | 79.14 | 6.77 | 2.09 | 4.79 | 79.12 | 6.79 | 2.1 | 4.8 | δ5.0-9.0 16H |
| | | | | | | | | | δ0.5-4.5 29H |
| 24 | 78.13 | 6.99 | 1.91 | 4.32 | 78.12 | 6.97 | 1.9 | 4.34 | δ5.0-9.0 16H |
| | | | | | | | | | δ0.5-4.5 35H |
| 25 | 79.96 | 7.26 | 1.92 | 4.39 | 79.96 | 7.26 | 1.9 | 4.36 | δ5.0-9.0 16H |
| | | | | | | | | | δ0.5-4.5 37H |
| 26 | 79.37 | 7.09 | 1.99 | 4.59 | 79.39 | 7.1 | 2.01 | 4.61 | δ5.0-9.0 16H |
| | | | | | | | | | δ0.5-4.5 33H |
| 27 | 82.35 | 6.66 | 0 | 4.38 | 82.38 | 6.64 | 0 | 4.4 | δ5.0-9.0 21H |
| | | | | | | | | | δ0.5-4.5 27H |
| 28 | 80.6 | 6.51 | 0 | 4.28 | 80.61 | 6.49 | 0 | 4.3 | δ5.0-9.0 16H |
| | | | | | | | | | δ0.5-4.5 32H |
| 29 | 79.03 | 6.65 | 0 | 4.77 | 79.01 | 6.63 | 0 | 4.79 | δ5.0-9.0 16H |
| | | | | | | | | | δ0.5-4.5 28H |
| 30 | 81.05 | 6.93 | 0 | 4.8 | 81.04 | 6.95 | 0 | 4.81 | δ5.0-9.0 16H |
| | | | | | | | | | δ0.5-4.5 30H |
| 31 | 78.16 | 6.95 | 1.88 | 4.31 | 78.12 | 6.97 | 1.9 | 4.34 | δ5.0-9.0 16H |
| | | | | | | | | | δ0.5-4.5 35H |
| 32 | 79.04 | 6.63 | 0 | 4.38 | 79.01 | 6.63 | 0 | 4.39 | δ5.0-9.0 16H |
| | | | | | | | | | δ0.5-4.5 28H |
| 33 | 75.74 | 5.69 | 0 | 10.66 | 75.71 | 5.69 | 0 | 10.64 | δ5.0-9.0 16H |
| | | | | | | | | | δ0.5-4.5 18H |
| 34 | 73.5 | 5.32 | 0 | 10.63 | 73.48 | 5.33 | 0 | 10.6 | δ5.0-9.0 16H |
| | | | | | | | | | δ0.5-4.5 16H |
| 35 | 73.78 | 5.56 | 0 | 10.35 | 73.76 | 5.54 | 0 | 10.36 | δ5.0-9.0 16H |
| | | | | | | | | | δ0.5-4.5 18H |
| 36 | 76.99 | 6.34 | 0 | 9.55 | 76.98 | 6.31 | 0 | 9.56 | δ5.0-9.0 16H |
| | | | | | | | | | δ0.5-4.5 26H |
| 37 | 76.61 | 5.97 | 0 | 9.94 | 76.6 | 5.96 | 0 | 9.98 | δ5.0-9.0 16H |
| | | | | | | | | | δ0.5-4.5 22H |
| 38 | 77.14 | 6.45 | 0 | 9.35 | 77.15 | 6.47 | 0 | 9.36 | δ5.0-9.0 16H |
| | | | | | | | | | δ0.5-4.5 28H |
| 39 | 77.17 | 6.48 | 0 | 9.34 | 77.15 | 6.47 | 0 | 9.36 | δ5.0-9.0 16H |
| | | | | | | | | | δ0.5-4.5 28H |
| 40 | 77.04 | 5.86 | 0 | 9.82 | 77.03 | 5.85 | 0 | 9.79 | δ5.0-9.0 16H |
| | | | | | | | | | δ0.5-4.5 22H |
| 41 | 72.01 | 5.94 | 0.00 | 8.34 | 72.04 | 5.91 | 0.00 | 8.36 | δ5.0-9.0 15H |
| | | | | | | | | | δ0.5-4.5 30H |
| 42 | 75.95 | 5.97 | 2.00 | 9.19 | 75.94 | 5.94 | 2.01 | 9.21 | δ5.0-9.0 15H |
| | | | | | | | | | δ0.5-4.5 26H |
| 43 | 76.44 | 6.84 | 1.84 | 8.48 | 76.46 | 6.82 | 1.86 | 8.50 | δ5.0-9.0 16H |
| | | | | | | | | | δ0.5-4.5 36H |
| 44 | 77.99 | 6.82 | 1.91 | 8.89 | 77.97 | 6.82 | 1.93 | 8.86 | δ5.0-9.0 17H |
| | | | | | | | | | δ0.5-4.5 32H |
| 45 | 79.13 | 6.77 | 0.00 | 9.40 | 79.14 | 6.79 | 0.00 | 9.39 | δ5.0-9.0 16H |
| | | | | | | | | | δ0.5-4.5 30H |
| 46 | 78.98 | 6.61 | 0.00 | 9.57 | 79.00 | 6.63 | 0.00 | 9.59 | δ5.0-9.0 17H |
| | | | | | | | | | δ0.5-4.5 27H |
| 47 | 77.76 | 5.82 | 0.00 | 5.50 | 77.79 | 5.84 | 0.00 | 5.46 | δ5.0-9.0 16H |
| | | | | | | | | | δ0.5-4.5 18H |
| 48 | 73.51 | 5.31 | 0.00 | 10.00 | 73.48 | 5.33 | 0.00 | 10.60 | δ5.0-9.0 16H |
| | | | | | | | | | δ0.5-4.5 16H |
| 49 | 76.32 | 6.25 | 1.92 | 4.44 | 76.32 | 6.27 | 1.93 | 4.43 | δ5.0-9.0 15H |
| | | | | | | | | | δ0.5-4.5 30H |

Examples 50 to 88

Photochromic plastic lenses were manufactured and their characteristic properties were evaluated in the same manner as in Example 6 except that the compounds obtained in Examples 11 to 49 were used as chromene compounds. The results are shown in Table 8. In Table 8, the compound Nos. 11 to 49 are chromene compounds obtained in Examples 11 to 49, respectively.

TABLE 8

| Example No. | Compound No. | λmax (nm) | Color optical density $A_0$ | Double peak characteristic $A_F/A_B$ | Fading half period $\tau_{1/2}$ (sec) | Initial coloration (absorption end) (nm) | Initial coloration (thermochromism) (%) | Residual rate $(A_{50}/A_0) \times 100$ (%) |
|---|---|---|---|---|---|---|---|---|
| 50 | 11 | 453 | 0.39 | 1.18 | 42 | 404 | 90 | 84 |
|  |  | 564 | 0.33 |  | 43 |  | 90 | 84 |
| 51 | 12 | 464 | 0.60 | 1.50 | 61 | 404 | 89 | 84 |
|  |  | 573 | 0.40 |  | 60 |  | 89 | 84 |
| 52 | 13 | 436 | 0.34 | 1.17 | 41 | 397 | 90 | 89 |
|  |  | 555 | 0.29 |  | 40 |  | 90 | 89 |
| 53 | 14 | 464 | 0.63 | 1.54 | 54 | 405 | 89 | 83 |
|  |  | 575 | 0.41 |  | 54 |  | 88 | 83 |
| 54 | 15 | 479 | 0.66 | 1.53 | 66 | 411 | 88 | 81 |
|  |  | 579 | 0.43 |  | 65 |  | 88 | 81 |
| 55 | 16 | 474 | 0.58 | 1.38 | 63 | 411 | 87 | 81 |
|  |  | 576 | 0.42 |  | 63 |  | 87 | 81 |
| 56 | 17 | 438 | 0.38 | 1.19 | 42 | 399 | 90 | 88 |
|  |  | 557 | 0.32 |  | 41 |  | 90 | 88 |
| 57 | 18 | 466 | 0.60 | 1.46 | 54 | 406 | 89 | 84 |
|  |  | 570 | 0.41 |  | 54 |  | 89 | 83 |
| 58 | 19 | 454 | 0.37 | 1.12 | 41 | 404 | 90 | 84 |
|  |  | 565 | 0.33 |  | 41 |  | 90 | 83 |
| 59 | 20 | 481 | 0.63 | 1.54 | 69 | 412 | 87 | 81 |
|  |  | 580 | 0.41 |  | 69 |  | 87 | 81 |
| 60 | 21 | 467 | 0.44 | 1.26 | 47 | 398 | 86 | 85 |
|  |  | 576 | 0.35 |  | 47 |  | 86 | 85 |
| 61 | 22 | 469 | 0.48 | 1.37 | 47 | 399 | 86 | 85 |
|  |  | 578 | 0.35 |  | 48 |  | 86 | 84 |
| 62 | 23 | 488 | 0.82 | 1.78 | 95 | 415 | 85 | 82 |
|  |  | 592 | 0.46 |  | 95 |  | 85 | 83 |
| 63 | 24 | 485 | 0.80 | 1.82 | 87 | 413 | 85 | 84 |
|  |  | 590 | 0.44 |  | 87 |  | 85 | 83 |
| 64 | 25 | 490 | 0.83 | 1.77 | 96 | 415 | 85 | 83 |
|  |  | 592 | 0.47 |  | 96 |  | 84 | 83 |
| 65 | 26 | 490 | 0.83 | 1.80 | 95 | 411 | 84 | 83 |
|  |  | 594 | 0.46 |  | 96 |  | 84 | 83 |
| 66 | 27 | 460 | 0.44 | 1.26 | 47 | 415 | 86 | 84 |
|  |  | 575 | 0.35 |  | 46 |  | 85 | 85 |
| 67 | 28 | 484 | 0.63 | 1.58 | 74 | 408 | 85 | 83 |
|  |  | 585 | 0.40 |  | 73 |  | 84 | 83 |
| 68 | 29 | 485 | 0.65 | 1.63 | 78 | 410 | 86 | 84 |
|  |  | 587 | 0.40 |  | 78 |  | 86 | 83 |
| 69 | 30 | 456 | 0.48 | 1.33 | 48 | 409 | 87 | 84 |
|  |  | 560 | 0.36 |  | 48 |  | 88 | 84 |
| 70 | 31 | 473 | 0.83 | 1.84 | 99 | 418 | 87 | 82 |
|  |  | 570 | 0.45 |  | 98 |  | 87 | 82 |
| 71 | 32 | 475 | 0.68 | 1.62 | 80 | 416 | 88 | 84 |
|  |  | 567 | 0.42 |  | 80 |  | 88 | 84 |
| 72 | 33 | 470 | 0.63 | 1.43 | 100 | 403 | 79 | 83 |
|  |  | 576 | 0.44 |  | 101 |  | 79 | 83 |
| 73 | 34 | 469 | 0.57 | 1.43 | 63 | 404 | 83 | 77 |
|  |  | 576 | 0.40 |  | 64 |  | 82 | 78 |
| 74 | 35 | 468 | 0.56 | 1.40 | 65 | 404 | 83 | 79 |
|  |  | 577 | 0.40 |  | 66 |  | 83 | 80 |
| 75 | 36 | 466 | 0.82 | 1.46 | 145 | 402 | 82 | 84 |
|  |  | 579 | 0.56 |  | 145 |  | 83 | 84 |
| 76 | 37 | 465 | 0.81 | 1.47 | 153 | 404 | 87 | 84 |
|  |  | 577 | 0.55 |  | 153 |  | 87 | 84 |
| 77 | 38 | 466 | 0.53 | 1.43 | 52 | 404 | 89 | 82 |
|  |  | 578 | 0.37 |  | 52 |  | 89 | 82 |
| 78 | 39 | 467 | 0.55 | 1.41 | 53 | 404 | 89 | 83 |
|  |  | 576 | 0.39 |  | 53 |  | 89 | 82 |
| 79 | 40 | 458 | 0.45 | 1.73 | 53 | 405 | 86 | 83 |
|  |  | 576 | 0.26 |  | 54 |  | 86 | 83 |
| 80 | 41 | 466 | 0.41 | 1.46 | 32 | 404 | 89 | 82 |
|  |  | 575 | 0.28 |  | 32 |  | 89 | 82 |
| 81 | 42 | 465 | 0.54 | 1.42 | 87 | 403 | 89 | 81 |
|  |  | 575 | 0.38 |  | 87 |  | 90 | 81 |
| 82 | 43 | 486 | 0.38 | 0.96 | 46 | 403 | 89 | 85 |
|  |  | 588 | 0.40 |  | 46 |  | 89 | 86 |
| 83 | 44 | 485 | 0.41 | 1.03 | 48 | 403 | 89 | 85 |
|  |  | 587 | 0.40 |  | 48 |  | 89 | 85 |

TABLE 8-continued

| Example No. | Compound No. | λmax (nm) | Color optical density $A_0$ | Double peak characteristic $A_Y/A_B$ | Fading half period $\tau^{1/2}$ (sec) | Initial coloration (absorption end) (nm) | Initial coloration (thermochromism) (%) | Residual rate $(A_{50}/A_0) \times 100$ (%) |
|---|---|---|---|---|---|---|---|---|
| 84 | 45 | 447 | 0.76 | 1.69 | 114 | 405 | 83 | 65 |
|  |  | 566 | 0.45 |  | 116 |  | 83 | 65 |
| 85 | 46 | 446 | 0.81 | 1.80 | 136 | 404 | 82 | 61 |
|  |  | 566 | 0.45 |  | 136 |  | 82 | 60 |
| 86 | 47 | 473 | 0.86 | 1.51 | 166 | 397 | 87 | 88 |
|  |  | 580 | 0.57 |  | 166 |  | 86 | 88 |
| 87 | 48 | 449 | 0.83 | 1.77 | 150 | 405 | 75 | 55 |
|  |  | 568 | 0.47 |  | 150 |  | 74 | 54 |
| 88 | 49 | 458 | 0.48 | 1.78 | 54 | 406 | 86 | 84 |
|  |  | 573 | 0.27 |  | 54 |  | 86 | 84 |

Examples of naphthol compound are as following.

Example 89

55.1 g (324.2 mmol) of a benzene compound represented by the above formula (11) was added dropwise to a dichloromethane solution (350 ml) of 51.8 g (388.6 mmol) of aluminum chloride and 45.6 g (324.3 mmol) of benzoyl chloride cooled to 0° C. After the end of addition, they were stirred for 2 hours. After the reaction, the reaction solution was washed in water, the solvent was removed, and the obtained product was purified by column chromatography to obtain a benzophenone derivative represented by the following formula (22) as 63.1 g (230.4 mmol, yield rate of 71%) of a yellow solid.

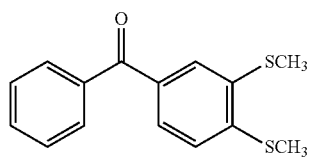

(22)

The benzophenone derivative of the above formula (22) and 46.2 g (265.0 mmol) of diethyl succinate were dissolved in 250 ml of tetrahydrofuran and heated to 55° C. A tetrahydrofuran solution (250 ml) of 29.7 g (265.0 mmol) of potassium-t-butoxide was added dropwise to this solution and stirred for 1 hour. After the reaction, the reaction solution was washed with concentrated hydrochloride acid and then with water, and the solvent was removed to obtain a compound represented by the following formula (23) as 92.6 g (230.4 mmol; yield rate of 100%) of an orange oil.

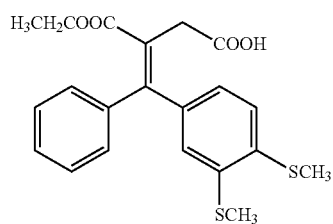

(23)

The compound of the above formula (23), 18.9 g (230.4 mmol) of sodium acetate and 118.7 g (1152.0 mmol) of acetic anhydride were dissolved in 300 ml of toluene and refluxed for 3 hours. After the reaction, the reaction solution was washed in water, the solvent was removed, and the obtained product was purified by recrystallization with methanol to obtain a compound represented by the following formula (24) as 22.6 g (53.0 mmol; yield rate of 23%) of an orange solid.

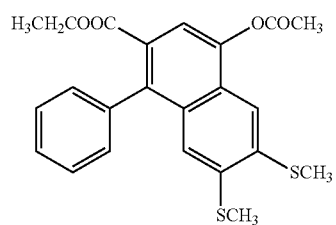

(24)

The compound of the above formula (24) was dispersed into 100 ml of methanol. 127 ml of an aqueous solution of 12.7 g (318.0 mmol) of sodium hydroxide was added to this solution and refluxed for 3 hours. After the reaction, the reaction solution was washed with concentrated hydrochloric acid and then with water, the solvent was removed, and the obtained product was purified by reslurrying with toluene to obtain a carboxylic acid derivative represented by the following formula (25) as 17.4 g (48.8 mmol, yield rate of 92%) of a yellow solid.

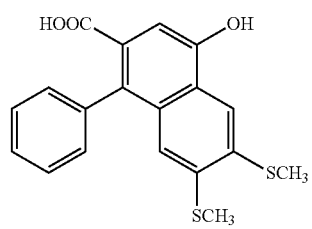

(25)

The carboxylic acid derivative of the above formula (25) and 14.8 g (107.4 mmol) of benzyl chloride were dissolved in 150 ml of N,N-dimethylformamide. 15.4 g (122.0 mmol) of potassium carbonate was added to this solution, heated to 60° C. and stirred for 3 hours. After the reaction, the reaction solution was washed in water, and the solvent was removed to obtain a compound represented by the following formula (26) as 24.1 g (44.9 mmol, yield rate of 92%) of a yellow oil.

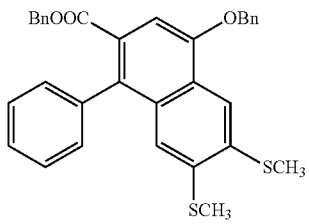

(26)

The compound of the above formula (26) was dispersed into 400 ml of isopropyl alcohol. 150 ml of an aqueous solution of 30.0 g (750.0 mmol) of sodium hydroxide was added to this solution and refluxed for 3 hours. After the reaction, the reaction solution was washed with concentrated hydrochloric acid and then with water, the solvent was removed, and the obtained product was purified by reslurrying with toluene to obtain a carboxylic acid derivative represented by the following formula (27) as 19.9 g (44.5 mmol, yield rate of 99%) of a yellow solid.

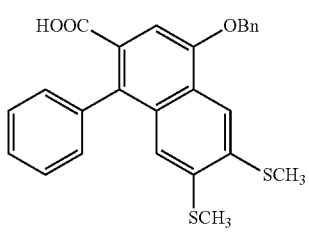

(27)

The carboxylic acid derivative of the above formula (27) was dispersed into 300 ml of toluene. 90.0 g (891.1 mmol) of triethylamine and 15.9 g (57.9 mmol) of diphenylphosphorylazide were added to this solution and stirred at room temperature for 2 hours. 20.0 g (435.3 mmol) of ethanol was added to this solution to carry out a reaction at 70° C. for 2 hours. Thereafter, 500 ml of ethanol was added to this solution, and then 74.7 g (1335.0 mmol) of potassium hydroxide was added and refluxed for 6 hours. After the reaction, ethanol was distilled off at normal pressure, tetrahydrofuran was added, the solution was washed in water, and the solvent was removed to obtain a compound represented by the following formula (28) as 15.8 g (37.8 mmol, yield rate of 85%) of a yellow solid.

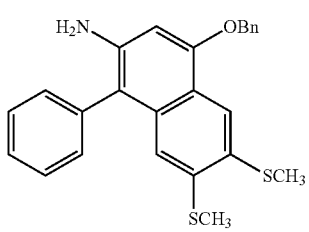

(28)

The compound of the above formula (28) was dispersed into 350 ml of acetonitrile, and 113.7 g (187.1 mmol) of a 6% hydrochloric acid aqueous solution was added to the dispersion and cooled to 0 to 5° C. 11.7 g (56.7 mmol) of a 33% sodium nitrite aqueous solution was added to this solution and stirred for 30 minutes. 47.1 g (283.5 mmol) of a 50% potassium iodide aqueous solution was added to this solution and stirred at room temperature for 5 hours. After the reaction, toluene was added, the reaction solution was washed in water, the solvent was removed, and the obtained product was purified by column chromatography to obtain a compound represented by the following formula (29) as 15.8 g (29.9 mmol, yield rate of 79%) of a yellow solid.

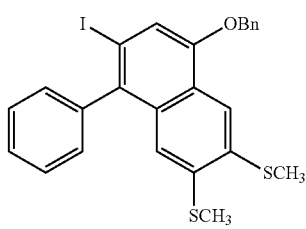

(29)

The compound of the above formula (29) was dispersed into 600 ml of toluene and cooled to −30° C. 28.1 ml (44.9 mmol) of n-butyl lithium (1.6M hexane solution) was added dropwise to this solution and stirred for 30 minutes. 14.8 g of a toluene solution of 7.4 g (47.8 mmol) of 3,3,5,5-tetramethylcyclohexanone was added dropwise to this solution and stirred at 0° C. for 3 hours. After the reaction, toluene was added, the reaction solution was washed in water, the solvent was removed, and the obtained product was purified by reslurrying with methanol to obtain a compound represented by the following formula (30) as 10.1 g (18.2 mmol, yield rate of 61%) of a yellow solid.

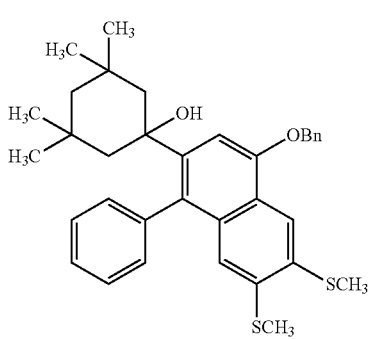

(30)

The compound of the above formula (30) and 221.1 mg (0.9 mmol) of (±)-10-camphorsulfonic acid were dissolved in 150 ml of toluene and refluxed for 30 minutes. The resulting solution was left to be cooled to room temperature, added to 100 ml of a toluene solution of 4.5 g (27.3 mmol) of p-toluenesulfonic acid heated at 90° C. and refluxed for 4 hours. After the reaction, the reaction solution was washed in water, the solvent was removed, and the obtained product was purified by column chromatography to obtain a naphthol compound represented by the following formula (31) as 3.7 g (8.2 mmol, yield rate of 45%) of a yellow solid.

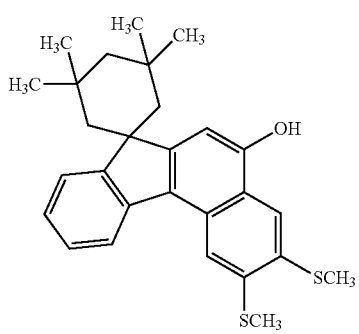

(31)

The elemental analysis values of this product were 74.91% of C, 7.21% of H and 14.30% of S which were almost equal to the calculated values of $C_{28}H_{32}OS_2$ (C, 74.95%; H, 7.19%; S, 14.29%).

When the proton nuclear magnetic resonance spectrum was measured, it showed a 24H peak based on an alkyl group at δ of around 0.5 to 4.5 ppm and a 7H peak based on an aromatic proton at δ of around 5.0 to 9.0 ppm Further, when the $^{13}$C-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (31).

This compound is a naphthol compound used in the above Example 3.

Example 90

When the operation of Example 89 was repeated by using 50.0 g (324.6 mmol) of the benzene compound represented by the above formula (10a), a naphthol compound represented by the following formula (32) was obtained as 4.0 g (9.3 mmol, yield rate of 2.8%) of a yellow solid.

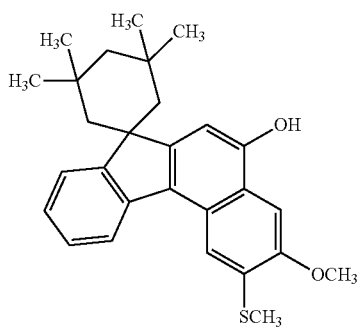

(32)

The elemental analysis values of this product were 77.79% of C, 7.50% of H and 7.37% of S which were almost equal to the calculated values of $C_{28}H_{32}O_2S$ (C, 77.74%; H, 7.46%; S, 7.41%).

When the proton nuclear magnetic resonance spectrum was measured, it showed a 24H peak based on an alkyl group at δ of around 0.5 to 4.5 ppm and a 7H peak based on an aromatic proton at δ of around 5.0 to 9.0 ppm Further, when the $^{13}$C-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from the above results that the isolated product was a compound represented by the above formula (32).

This compound is a naphthol compound used in the above Example 1.

Example 91

When the operation of Example 89 was repeated by using 55.0 g (348.1 mmol) of the benzene compound represented by the above formula (10b), a benzophenone derivative represented by the following formula (33) was obtained as 63.8 g (243.7 mmol, yield rate of 70%) of a yellow solid.

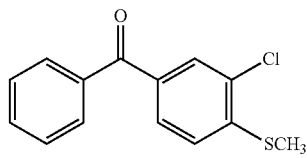

(33)

The benzophenone derivative of the above formula (33), 46.8 g (487.4 mmol) of sodium-t-butoxide, 4.5 g (4.9 mmol) of tris(dibenzylideneacetone)dipalladium, 3.5 g (7.3 mmol) of 1,1'-bis(di-t-butylphosphino)ferrocene and 31.8 g (365.5 mmol) of morpholine were dissolved in 650 ml of toluene and refluxed for 3 hours. After the reaction, the reaction solution was washed in water, the solvent was removed, and the obtained product was purified by column chromatography to obtain a benzophenone derivative represented by the following formula (34) as 47.3 g (151.1 mmol, yield rate of 62%) of a yellow solid.

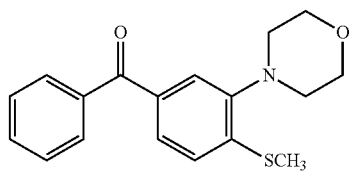

(34)

When the operation of Example 89 was repeated by using the benzene derivative represented by the above formula (34), a naphthol compound represented by the following formula (35) was obtained as 4.2 g (8.6 mmol, yield rate of 2.5%) of a yellow solid.

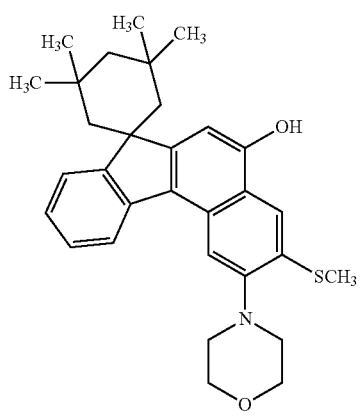

(35)

The elemental analysis values of this product were 76.39% of C, 7.61% of H, 2.85% of N and 6.57% of S which were almost equal to the calculated values of $C_{31}H_{37}NO_2S$(C, 76.35%; H, 7.65%; N, 2.87% and S, 6.57%).

When the proton nuclear magnetic resonance spectrum was measured, it showed a 24H peak based on an alkyl group at δ of around 0.5 to 4.5 ppm and a 7H peak based on an aromatic proton at δ of around 5.0 to 9.0 ppm Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (35).

This compound is a naphthol compound used in the above Example 24.

Examples 92 to 127

Naphthol compounds shown in the table were synthesized in the same manner as in Example 89. When the structures of the obtained products were analyzed by using the same structure checking means as in Example 89, it was confirmed that they were naphthol compounds used in Examples shown in Table 8. Table 9 shows the elemental analysis values of these compounds, the calculated values obtained from the structural formulas of the compounds and characteristic $^1$H-NMR spectra.

TABLE 9

| Example No. | Example No. of chromene compounds* | Elemental analysis values | | | | | | | | $^1$H-NMR (NMR) |
|---|---|---|---|---|---|---|---|---|---|---|
| | | Experimental values | | | | Calculated values | | | | |
| | | C | H | N | S | C | H | N | S | |
| 92 | 2 | 77.72 | 7.44 | 0.00 | 7.43 | 77.74 | 7.46 | 0.00 | 7.41 | δ5.0-9.0 7H<br>δ0.5-4.5 24H |
| 93 | 4 | 74.93 | 6.01 | 0.00 | 9.53 | 74.97 | 5.99 | 0.00 | 9.53 | δ5.0-9.0 7H<br>δ0.5-4.5 13H |
| 94 | 5 | 68.08 | 5.52 | 0.00 | 6.98 | 68.10 | 5.50 | 0.00 | 6.99 | δ5.0-9.0 7H<br>δ0.5-4.5 18H |
| 95 | 11 | 74.64 | 6.99 | 0.00 | 12.77 | 74.61 | 6.96 | 0.00 | 14.75 | δ5.0-9.0 7H<br>δ0.5-4.5 23H |
| 96 | 12 | 72.78 | 7.15 | 0.00 | 13.37 | 72.76 | 7.16 | 0.00 | 13.40 | δ5.0-9.0 7H<br>δ0.5-4.5 27H |
| 97 | 13 | 66.88 | 5.79 | 0.00 | 12.75 | 66.90 | 5.82 | 0.00 | 12.76 | δ5.0-9.0 7H<br>δ0.5-4.5 22H |
| 98 | 14 | 76.71 | 7.78 | 0.00 | 12.39 | 76.69 | 7.80 | 0.00 | 12.41 | δ5.0-9.0 7H<br>δ0.5-4.5 33H |
| 99 | 15 | 77.61 | 6.71 | 0.00 | 12.58 | 77.60 | 6.71 | 0.00 | 12.56 | δ5.0-9.0 12H<br>δ0.5-4.5 22H |
| 100 | 16 | 72.04 | 6.23 | 0.00 | 18.59 | 72.05 | 6.24 | 0.00 | 18.61 | δ5.0-9.0 10H<br>δ0.5-4.5 22H |
| 101 | 17 | 66.88 | 5.84 | 0.00 | 12.79 | 66.90 | 5.82 | 0.00 | 12.76 | δ5.0-9.0 7H<br>δ0.5-4.5 22H |
| 102 | 18 | 76.70 | 7.82 | 0.00 | 12.43 | 76.69 | 7.80 | 0.00 | 12.41 | δ5.0-9.0 7H<br>δ0.5-4.5 33H |
| 103 | 19 | 74.59 | 6.98 | 0.00 | 14.77 | 74.61 | 6.96 | 0.00 | 14.75 | δ5.0-9.0 7H<br>δ0.5-4.5 23H |
| 104 | 20 | 77.58 | 6.73 | 0.00 | 12.58 | 77.60 | 6.71 | 0.00 | 12.56 | δ5.0-9.0 12H<br>δ0.5-4.5 22H |
| 105 | 21 | 80.77 | 7.75 | 0.00 | 7.68 | 80.72 | 7.74 | 0.00 | 7.70 | δ5.0-9.0 7H<br>δ0.5-4.5 25H |
| 106 | 22 | 81.74 | 8.32 | 0.00 | 6.64 | 81.77 | 8.32 | 0.00 | 6.61 | δ5.0-9.0 7H<br>δ0.5-4.5 33H |
| 107 | 23 | 77.67 | 7.46 | 3.33 | 7.67 | 77.65 | 7.48 | 3.35 | 7.68 | δ5.0-9.0 7H<br>δ0.5-4.5 24H |
| 108 | 25 | 79.14 | 8.07 | 2.87 | 6.58 | 79.13 | 8.09 | 2.88 | 6.60 | δ5.0-9.0 7H<br>δ0.5-4.5 32H |
| 109 | 26 | 78.16 | 7.91 | 3.16 | 7.21 | 78.16 | 7.92 | 3.14 | 7.19 | δ5.0-9.0 7H<br>δ0.5-4.5 28H |
| 110 | 27 | 82.80 | 7.18 | 0.00 | 6.69 | 82.80 | 7.16 | 0.00 | 6.70 | δ5.0-9.0 12H<br>δ0.5-4.5 22H |
| 111 | 28 | 80.10 | 6.93 | 0.00 | 6.51 | 80.12 | 6.93 | 0.00 | 6.48 | δ5.0-9.0 12H<br>δ0.5-4.5 22H |
| 112 | 29 | 77.46 | 7.24 | 0.00 | 7.65 | 77.47 | 7.22 | 0.00 | 7.66 | δ5.0-9.0 7H<br>δ0.5-4.5 23H |
| 113 | 30 | 80.74 | 7.75 | 0.00 | 7.72 | 80.72 | 7.74 | 0.00 | 7.70 | δ5.0-9.0 7H<br>δ0.5-4.5 25H |
| 114 | 31 | 76.74 | 7.64 | 2.85 | 6.56 | 76.75 | 7.65 | 2.87 | 6.57 | δ5.0-9.0 7H<br>δ0.5-4.5 30H |
| 115 | 32 | 77.48 | 7.23 | 0.00 | 7.64 | 77.47 | 7.22 | 0.00 | 7.66 | δ5.0-9.0 7H<br>δ0.5-4.5 23H |
| 116 | 33 | 71.58 | 5.71 | 0.00 | 18.16 | 71.55 | 5.72 | 0.00 | 18.19 | δ5.0-9.0 7H<br>δ0.5-4.5 13H |
| 117 | 34 | 67.79 | 5.14 | 0.00 | 18.11 | 67.76 | 5.12 | 0.00 | 18.09 | δ5.0-9.0 7H<br>δ0.5-4.5 11H |
| 118 | 35 | 68.43 | 5.49 | 0.00 | 17.39 | 68.44 | 5.47 | 0.00 | 17.40 | δ5.0-9.0 7H<br>δ0.5-4.5 13H |

TABLE 9-continued

| Example No. | Example No. of chromene compounds* | Elemental analysis values | | | | | | | | $^1$H-NMR (NMR) |
|---|---|---|---|---|---|---|---|---|---|---|
| | | Experimental values | | | | Calculated values | | | | |
| | | C | H | N | S | C | H | N | S | |
| 119 | 36 | 74.21 | 6.70 | 0.00 | 15.26 | 74.24 | 6.71 | 0.00 | 15.25 | δ5.0-9.0 6H δ0.5-4.5 22H |
| 120 | 37 | 73.42 | 6.14 | 0.00 | 16.36 | 73.43 | 6.16 | 0.00 | 16.34 | δ5.0-9.0 7H δ0.5-4.5 17H |
| 121 | 38 | 74.64 | 6.94 | 0.00 | 14.77 | 74.61 | 6.96 | 0.00 | 14.75 | δ5.0-9.0 7H δ0.5-4.5 23H |
| 122 | 39 | 74.61 | 6.96 | 0.00 | 14.76 | 74.61 | 6.96 | 0.00 | 14.75 | δ5.0-9.0 7H δ0.5-4.5 23H |
| 123 | 40 | 74.19 | 5.97 | 0.00 | 15.83 | 74.22 | 5.98 | 0.00 | 15.85 | δ5.0-9.0 7H δ0.5-4.5 17H |
| 124 | 41 | 67.38 | 6.03 | 0.00 | 12.44 | 67.41 | 6.05 | 0.00 | 12.41 | δ5.0-9.0 6H δ0.5-4.5 25H |
| 125 | 42 | 72.75 | 6.09 | 3.16 | 14.41 | 72.77 | 6.11 | 3.14 | 14.39 | δ5.0-9.0 6H δ0.5-4.5 21H |
| 126 | 47 | 74.96 | 6.02 | 0.00 | 9.55 | 74.97 | 5.99 | 0.00 | 9.53 | δ5.0-9.0 7H δ0.5-4.5 13H |
| 127 | 49 | 77.26 | 6.25 | 0.00 | 8.34 | 77.28 | 6.23 | 0.00 | 8.25 | δ5.0-9.0 7H δ0.5-4.5 17H |

*Examples of chromene compounds produced by using the naphthol compounds of Examples.

Examples 128 to 130

Photochromic plastic lenses were manufactured and their characteristic properties were evaluated in the same manner as in Example 6 except that the chromene compound (chromene compound No. 1) in Example 1 of the present invention was mixed with the following chromene compounds (36), (37) and (38) in ratios shown in Table 10. The results are shown in Table 11.

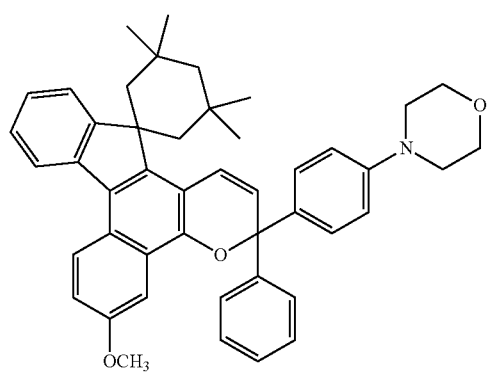

(36)

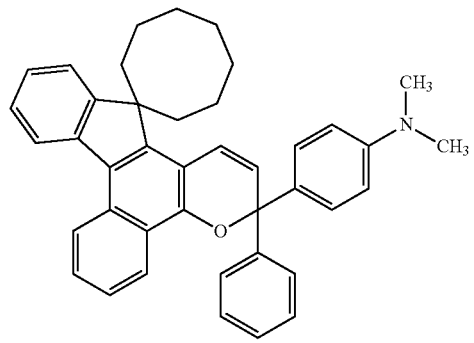

(37)

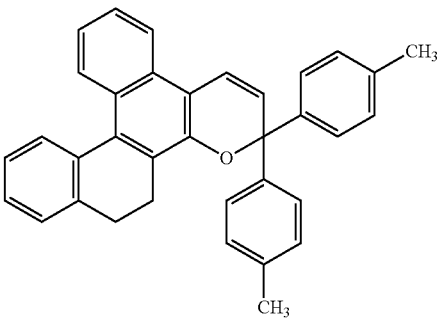

(38)

TABLE 10

| Example | Compound | Photo chromic compound | | | | |
|---|---|---|---|---|---|---|
| No. | No. | 1 | 36 | 37 | 38 | Color |
| 128 | Amount (parts by mass) | 2.0 | 0.5 | — | — | brown |
| 129 | Amount (parts by mass) | 2.5 | — | 0.7 | — | gray |
| 130 | Amount (parts by mass) | 2.0 | — | 0.2 | 0.4 | brown |

TABLE 11

| Example No. | λmax (nm) | Color optical density $A_0$ | Double peak characteristic $A_Y/A_B$ | Fading half period $\tau^{1/2}$ (sec) | Initial coloration (absorption end) (nm) | Initial coloration (thermochromism) (%) | Residual rate $(A_{50}/A_0) \times 100$ (%) |
|---|---|---|---|---|---|---|---|
| 128 | 468 | 0.99 | 1.14 | 51 | 416 | 89 | 81 |
|  | 575 | 0.87 |  | 52 |  | 89 | 80 |
| 129 | 464 | 1.15 | 1.00 | 52 | 410 | 88 | 80 |
|  | 576 | 1.15 |  | 61 |  | 88 | 78 |
| 130 | 460 | 1.10 | 1.62 | 50 | 409 | 88 | 76 |
|  | 575 | 0.68 |  | 60 |  | 87 | 79 |

As shown in Table 11, the photochromic plastic lenses which are obtained by curing the chromene compositions of the present invention have a transmittance by thermochromism of not less than 88%, the absorption end at 420 nm or less and very little initial coloration.

EFFECT OF THE INVENTION

The chromene compound of the present invention develops a color of a neutral tint and has little initial coloration, high color development sensitivity, high color optical density and a high fading speed even when it is dispersed into a solution or a polymer solid matrix as well as excellent durability.

Therefore, when a photochromic lens is manufactured by using the chromene compound of the present invention, it swiftly develops a dark color of a neutral tint when it moves outside and returns to its original color swiftly when it returns inside from outside and has such high durability that it can be used for a long time.

The invention claimed is:

1. A chromene compound having a skeleton represented by the following formula (2):

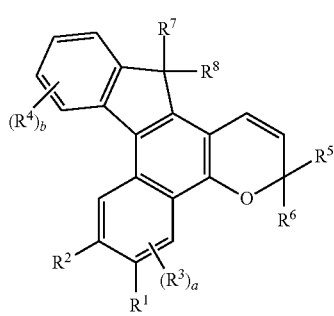

(2)

wherein (i) $R^1$ and $R^2$ are each a sulfur-containing substituent selected from the group consisting of thiol group, alkylthio group, alkoxyalkylthio group, haloalkylthio group, cycloalkylthio group, arylthio group and heteroarylthio group, (ii) $R^1$ is the above sulfur-containing substituent and $R^2$ is a hydrogen atom, hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group, or (iii) $R^2$ is the above sulfur-containing substituent and $R^1$ is a hydrogen atom, hydroxyl group, alkyl group, haloalkyl group, cycloalkyl group, alkoxy group, amino group, aliphatic heterocyclic group having a ring member nitrogen atom and bonded to the benzene ring to which the aliphatic heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group or aryloxy group;

$R^3$ and $R^4$ are each independently a hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group;

$R^5$ and $R^6$ are each independently a group represented by the following formula (3):

(3)

wherein $R^9$ is an aryl group or heteroaryl group, $R^{10}$ is a hydrogen atom, alkyl group or halogen atom, and m is an integer of 1 to 3, group represented by the following formula (4):

(4)

wherein $R^{11}$ is an aryl group or heteroaryl group, and n is an integer of 1 to 3, aryl group, heteroaryl group or alkyl group, and $R^5$ and $R^6$ may form an aliphatic hydrocarbon ring together with the carbon atom to which $R^5$ and $R^6$ bond;

$R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group, and $R^7$ and $R^8$ are bonded together to form an aliphatic ring having 3 to 20 ring member carbon atoms, condensed poly-ring having an aromatic ring or aromatic hetero ring condensed to the aliphatic ring, hetero ring having 3 to 20 ring member atoms, or condensed poly-ring having an aromatic ring or aromatic hetero ring condensed to the hetero ring, together with the 13-position carbon atom to which $R^7$ and $R^8$ bond, a is an integer of 0 to 2, b is an integer of 0 to 4, when a is 2, two $R^3$'s may be the same or different, and when b is 2 to 4, a plurality of $R^4$'s may be the same or different.

2. The chromene compound according to claim 1 which is represented by the following formula (5):

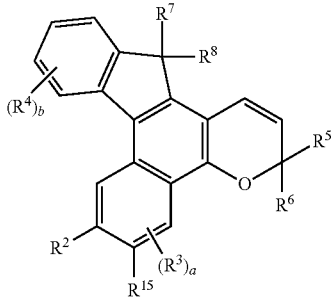

(5)

wherein $R^3$, $R^4$, $R^5$, $R^6$, $R^7$, $R^8$, a and b are as defined in the above formula (2), $R^2$ is the same as $R^2$ in (iii) in the above formula (2), and $R^{15}$ is an electron donor group having a Hammett constant $\sigma_p$ of −0.50 to −0.01 out of the groups defined as $R^1$ in (iii) in the above formula (2).

3. The chromene compound according to claim 1 which is represented by the following formula (6):

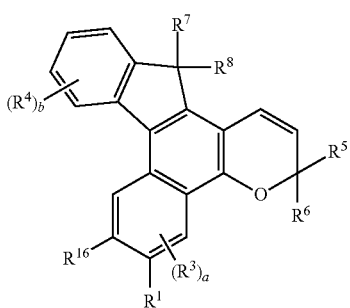

(6)

wherein $R^3$, $R^4$, $R^5$, $R^6$, $R^7$, $R^8$, a and b are as defined in the above formula (2), $R^1$ is the same as $R^1$ in (ii) in the above formula (2), and $R^{16}$ is an electron donor group having a Hammett constant $\sigma_p$ of −0.50 to −0.01 out of the groups defined as $R^2$ in (ii) in the above formula (2).

4. The chromene compound according to claim 1, wherein in the formula (2), (5) or (6), $R^7$ and $R^8$ form an aliphatic hydrocarbon ring together with the 13-position carbon atoms to which $R^7$ and $R^8$ bond, and the aliphatic hydrocarbon ring has 4 to 20 ring member carbon atoms and may have at least one substituent selected from the group consisting of alkyl group, haloalkyl group, cycloalkyl group, alkoxy group, amino group, aralkyl group, aryl group and halogen atom.

5. A photochromic curable composition comprising the chromene compound of claim 1 and a polymerizable monomer.

6. A photochromic optical article having a polymer molded product containing the chromene compound of claim 1 dispersed therein as a constituent member.

7. An optical article having an optical substrate all or part of at least one surface of which is coated with a polymer film comprising the chromene compound of claim 1 dispersed therein as a constituent member.

8. A naphthol compound represented by the following formula (7):

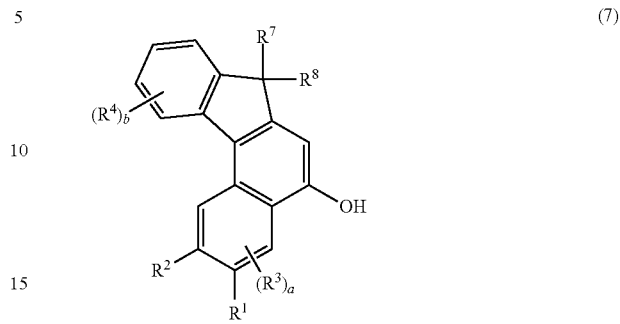

(7)

wherein (i) $R^1$ and $R^2$ are each a sulfur-containing substituent selected from the group consisting of thiol group, alkylthio group, alkoxyalkylthio group, haloalkylthio group, cycloalkylthio group, arylthio group and heteroarylthio group, (ii) $R^1$ is the above sulfur-containing substituent and $R^2$ is a hydrogen atom, hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group, or (iii) $R^2$ is the above sulfur-containing substituent and $R^1$ is a hydrogen atom, hydroxyl group, alkyl group, haloalkyl group, cycloalkyl group, alkoxy group, amino group, aliphatic heterocyclic group having a ring member nitrogen atom and bonded to the benzene ring to which the aliphatic heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group or aryloxy group;

$R^3$ and $R^4$ are each independently a hydroxyl group, alkyl group, haloalkyl group, cycloalkyl group, alkoxy group, amino group, heterocyclic group having a ring member nitrogen atom and bonded to the benzene ring to which the heterocyclic group bonds via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group;

$R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group, and $R^7$ and $R^8$ are bonded together to form an aliphatic ring having 3 to 20 ring member carbon atoms, condensed poly-ring having an aromatic ring or aromatic hetero ring condensed to the aliphatic ring, hetero ring having 3 to 20 ring member atoms, or condensed poly-ring having an aromatic ring or aromatic hetero ring condensed to the hetero ring, together with the 13-position carbon atom to which $R^7$ and $R^8$ bond, a is an integer of 0 to 2, b is an integer of 0 to 4, when a is 2, two $R^3$'s may be the same or different, and when b is 2 to 4, a plurality of $R^4$'s may be the same or different.

* * * * *